(12) United States Patent
Holt et al.

(10) Patent No.: US 12,062,453 B2
(45) Date of Patent: Aug. 13, 2024

(54) SELF-TITRATING BACTERIAL PROTEASE-ACTIVATED PRODRUG

(71) Applicant: GEORGIA TECH RESEARCH CORPORATION, Atlanta, GA (US)

(72) Inventors: Brandon Holt, Atlanta, GA (US); Gabriel Kwong, Atlanta, GA (US)

(73) Assignee: GEORGIA TECH RESEARCH CORPORATION, Atlanta, GA (US)

( * ) Notice: Subject to any disclaimer, the term of this patent is extended or adjusted under 35 U.S.C. 154(b) by 729 days.

(21) Appl. No.: 17/276,679

(22) PCT Filed: Sep. 19, 2019

(86) PCT No.: PCT/US2019/051816
§ 371 (c)(1),
(2) Date: Mar. 16, 2021

(87) PCT Pub. No.: WO2020/061244
PCT Pub. Date: Mar. 26, 2020

(65) Prior Publication Data
US 2022/0181034 A1 Jun. 9, 2022

Related U.S. Application Data

(60) Provisional application No. 62/733,347, filed on Sep. 19, 2018.

(51) Int. Cl.
*G06F 30/20* (2020.01)
*G16H 50/50* (2018.01)
*G06F 111/10* (2020.01)

(52) U.S. Cl.
CPC ............ *G16H 50/50* (2018.01); *G06F 30/20* (2020.01); *G06F 2111/10* (2020.01)

(58) Field of Classification Search
CPC ...... G06F 30/20; G06F 2111/10; G16H 50/50
(Continued)

(56) References Cited

U.S. PATENT DOCUMENTS

| 5,013,556 A | 5/1991 | Woodle et al. |
| 2007/0258996 A1* | 11/2007 | Mookerjee ............. A61K 36/67 514/711 |
| 2017/0088582 A1* | 3/2017 | Roberts ................ C07K 5/1008 |

FOREIGN PATENT DOCUMENTS

| EP | 3852786 A2 | 7/2021 |
| WO | 2005/030956 A1 | 4/2005 |

(Continued)

OTHER PUBLICATIONS

Allison, K.R., et al., "Metabolite-enabled eradication of bacterial persisters by aminoglycosides", Nature, 473: 216-220 (2011).
(Continued)

*Primary Examiner* — Andre Pierre Louis
(74) *Attorney, Agent, or Firm* — Meunier Carlin & Curfman LLC

(57) ABSTRACT

Disclosed herein are bacterial protease-activated prodrug compositions and methods of their use for the treatment and prevention of bacterial infection. Also disclosed are methods of reducing or eliminating defiant bacterial populations. An exemplary prodrug composition includes a cationic antimicrobial peptide conjugated to an anionic peptide with a protease cleavable linker substrate, wherein the antimicrobial peptide is inactive while it is in conjugation with the anionic peptide. Upon cleavage by the protease, the cationic AMP is released from the anionic peptide and can act upon bacteria. The protease is specific to the bacteria that are present in the sample or the subject, creating an auto-
(Continued)

titrating mechanism wherein the AMP is released from the peptide only when there is bacteria present.

8 Claims, 20 Drawing Sheets

Specification includes a Sequence Listing.

(58) Field of Classification Search
USPC .............................................. 703/2
See application file for complete search history.

(56) References Cited

FOREIGN PATENT DOCUMENTS

| WO | 2011/163012 A2 | 12/2011 |
|---|---|---|
| WO | 2012/035139 A1 | 3/2012 |
| WO | 2020/061244 A2 | 3/2020 |

OTHER PUBLICATIONS

Atuegwu, N.C., et al., "Parameterizing the Logistic Model of Tumor Growth by DW-MRI and DCE-MRI Data to Predict Treatment Response and Changes in Breast Cancer Cellularity during Neoadjuvant Chemotherapy", Translational Oncology, 6(3): 256-264 (2013).
Bailey, A.M., et al., "Dosing of Appropriate Antibiotics and Time to Administration of First Doses in the Pediatric Emergency Department", J. Pediatr. Pharmacol. Ther., 20(4): 309-315 (2015).
Baltzer, B., et al., "Mutual Pro-Drugs of β-Lactam Antibiotics and β-Lactamase Inhibitors", J. Antibiot., 33(10): 1183-1192 (1980).
Baquero, F., et al., "Antibiotics and antibiotic resistance in water environments", Current Opinion in Biotechnology, 19(3): 260-265 (2008).
Bielicki, J.A., et al., "Not too little, not too much: Problems of selecting oral antibiotic dose for children", British Medical Journal, 351: h5447 (2015).
Bradshaw, J.P., "Cationic Antimicrobial Peptides: Issues for Potential Clinical Use", BioDrugs, 17(4): 233-240 (2003).
Brannon, J.R., et al., "Inhibition of Outer Membrane Proteases of the Omptin Family by Aprotinin", Infection and Immunity, 83(6): 2300-2311 (2015).
Brauner, A., et al., "Distinguishing between resistance, tolerance, and persistence to antibiotic treatment", Nature Reviews Microbiology, 14: 320-330 (2016).
Cohen, N.R., et al., "Microbial persistence and the road to drug resistance", Cell Host & Microbe, 13(6): 632-642 (2013).
Communication Pursuant to Rules 161(2) and 162 EPC received in EP 19863483.4, issued on May 12, 2021 (3 pages).
International Search Report and Written Opinion issued for PCT/US2019/051816, received on Mar. 9, 2020 (8 pages).
Farewell, A., et al., "Effect of Temperature on In Vivo Protein Synthetic Capacity in *Escherichia coli*", Journal of Bacteriology, 180(17): 4704-4710 (1998).
Fujikawa, H., et al., "A New Logistic Model for Bacterial Growth", Journal of Food Hygienic Society of Japan, 44(3): 155-160 (2003).
Grodberg, J., et al, "ompT encodes the *Escherichia coli* outer membrane protease that cleaves T7 RNA polymerase during purification", Journal of Bacteriology, 170(3): 1245-1253 (1988).
Gullberg, E., et al., "Selection of Resistant Bacteria at Very Low Antibiotic Concentrations", PLOS Pathogens, 7(7): e1002158 (2011).

Holt, B.A., et al., "Fc microparticles can modulate the physical extent and magnitude of complement activity", Biomaterials Science, 5: 463-474 (2017).
Holt, B.A., et al., "Nanosensors to Detect Protease Activity In Vivo for Noninvasive Diagnostics", J. of Vis. Exp., 137: e57937 (2018).
Iizumi, T., et al., "Gut Microbiome and Antibiotics", Arch. Med. Res., 48(8): 727-734 (2017).
International Preliminary Report on Patentability issued for PCT/US2019/051816, received on Mar. 3, 2021 (5 pages).
Kapust, R.B., et al., "Tobacco etch virus protease: mechanism of autolysis and rational design of stable mutants with wild-type catalytic proficiency", Protein Engineering Design and Selection, 14(12): 993-1000 (2001).
Kwong, G.A., et al., "Mass-encoded synthetic biomarkers for multiplexed urinary monitoring of disease", Nat. Biotech., 31: 63-70 (2013).
Mac, Q.D., et al., "Non-invasive early detection of acute transplant rejection via nanosensors of granzyme?B activity", Nat. Biomed. Eng., 3: 281-291 (2019).
Mahlapuu, M., et al., "Antimicrobial Peptides: An Emerging Category of Therapeutic Agents", Frontiers in Cell. Infect. Microbiol., 6: 194 (2016).
Molina-Quiroz, R.C., et al., "Cyclic AMP Regulates Bacterial Persistence through Repression of the Oxidative Stress Response and SOS-Dependent DNA Repair in Uropathogenic *Escherichia coli*", mBio, 9(1): e02144-17 (2018).
Needham, D., et al., "A new temperature-sensitive liposome for use with mild hyperthermia: characterization and testing in a human tumor xenograft model", Cancer Research, 60(5): 1197-1201 (2000).
Newmark, J., et al., "Preparation and Properties of Adducts of Streptokinase and Streptokinase-Plasmin Complex with Polyethylene Glycol and Pluronic Polyol F38", J. Appl. Biochem., 4(2): 185-189 (1982).
Rautio, J., et al., "The expanding role of prodrugs in contemporary drug design and development", Nat. Rev. Drug Discov., 17(8): 559-587 (2018).
Roversi, D., et al., "How Many Antimicrobial Peptide Molecules Kill a Bacterium? The Case of PMAP-23", ACS Chemical Biology, 9: 2003-2007 (2014).
Thonus, I.P., et al., "Ampicillin susceptibility and ampicillin-induced killing rate of *Escherichia coli*.", Antimicrobial Agents and Chemotherapy, 22: 386-390 (1982).
Wimley, W.C., et al., "Antimicrobial peptides: successes, challenges and unanswered questions", J. Membr. Biol., 239(1-2): 27-34 (2011).
Zhuang, Q., et al., "Deconvolving multiplexed protease signatures with substrate reduction and activity clustering", bioRxiv, 564906 (2019).
Extended European Search Report for Application No. 19863483.4 dated Aug. 26, 2022, 15 pages.
Forde et al., "Pro-Moieties of Antimicrobial Peptide Prodrugs," Molecules, vol. 20, No. 1, Jan. 1, 2015, pp. 1210-1227.
Murphy et al., "A Theoretical Analysis of the Prodrug Delivery System for Treating Antibiotic-Resistant Bacteria," IEEE/ACM Transactions on Computational Biology and Bioinformatics, IEEE Service Center, New York, NY, US, vol. 8, No. 3, May 1, 2011, pp. 650-658.
Fleck et al., "A screen for and validation of prodrug antimicrobials," Antimicrobial Agents and Chemotherapy American Society for Microbiology, US, vol. 58, No. 3, Jan. 1, 2014, pp. 1410-1419.
Holt et al., "Bacterial defiance as a form of prodrug failure," bioRxiv, Feb. 26, 2019.

\* cited by examiner

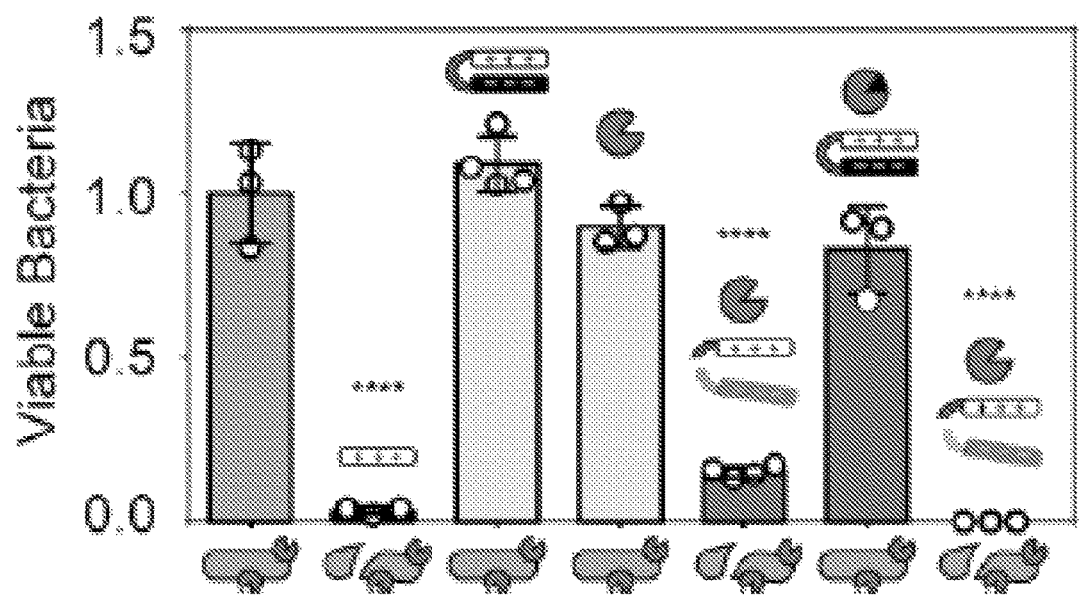
FIG. 1I
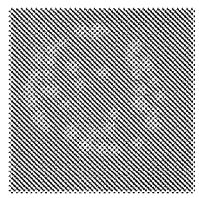 Bacteria 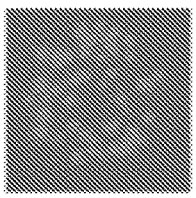  +inhibitor +AMP prodrug
FIG. 1J    FIG. 1K
 + AMP    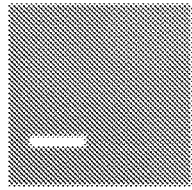  +AMP prodrug
FIG. 1L    FIG. 1M

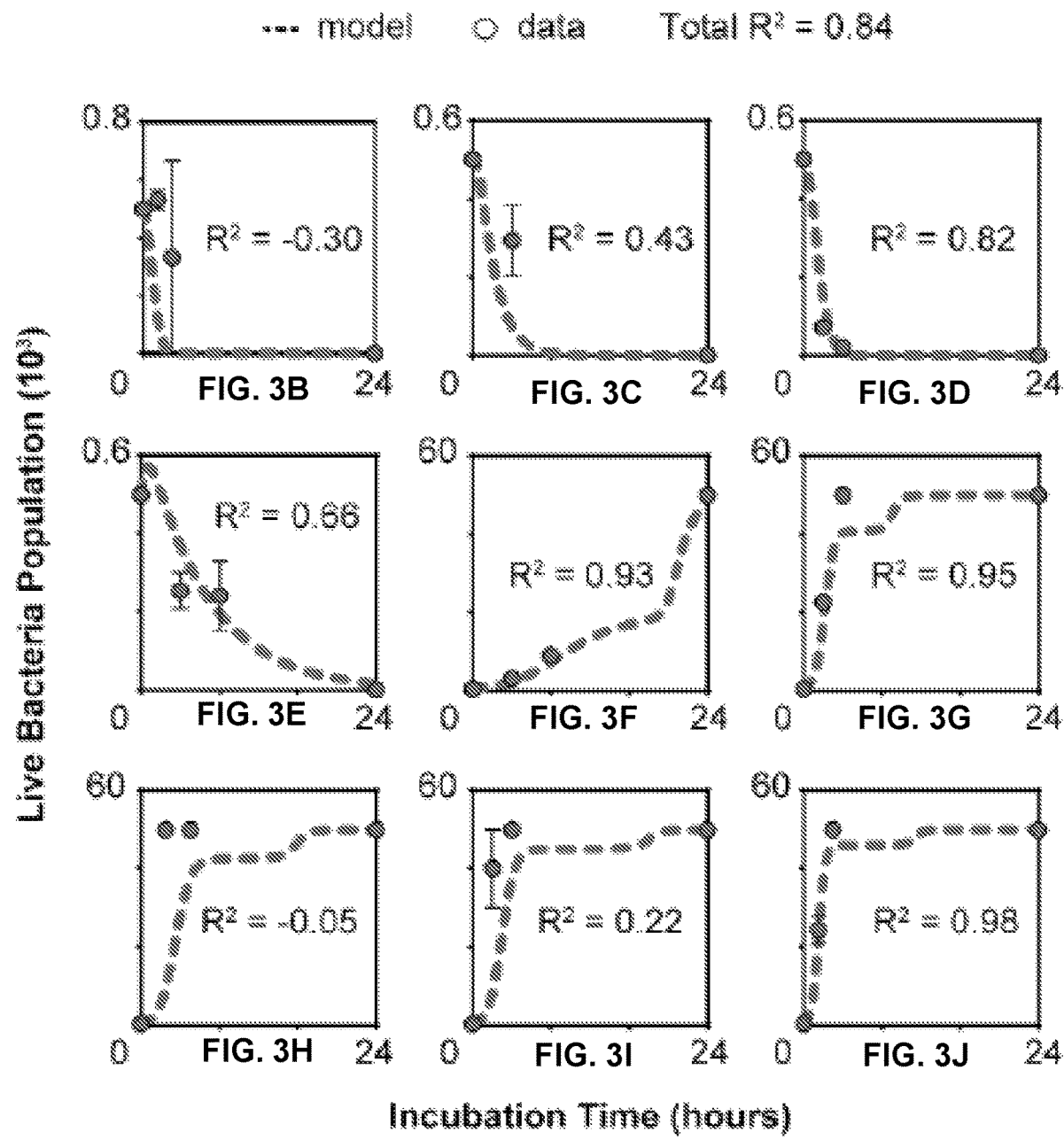

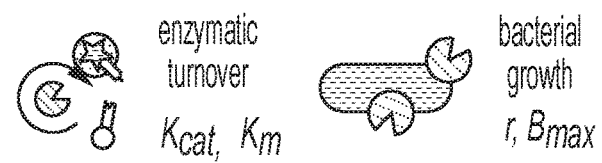
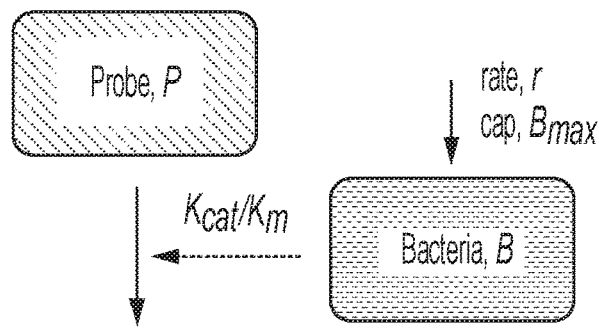
FIG. 5A
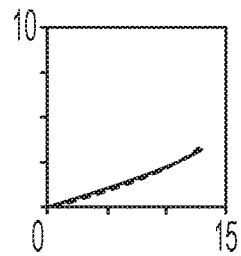
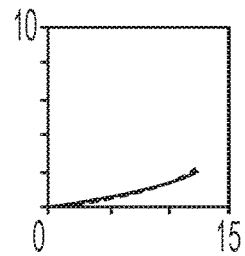
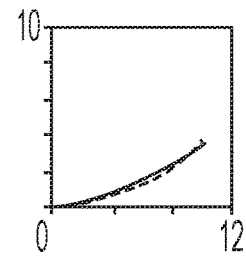
FIG. 5B    FIG. 5C    FIG. 5D
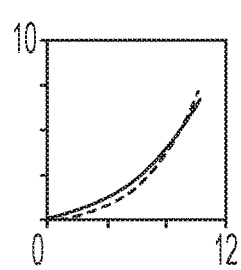
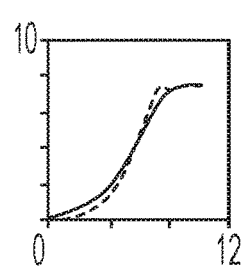
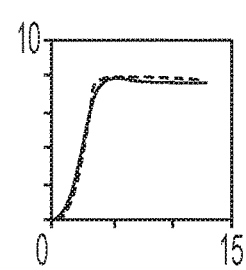
FIG. 5E    FIG. 5F    FIG. 5G
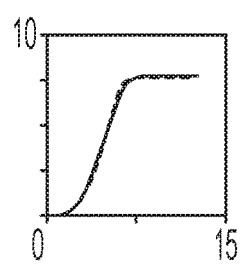
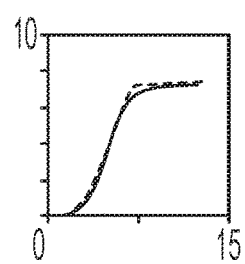
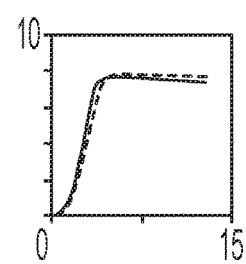
FIG. 5H    FIG. 5I    FIG. 5J
Incubation Time (hours)
FIGS. 5B-5J

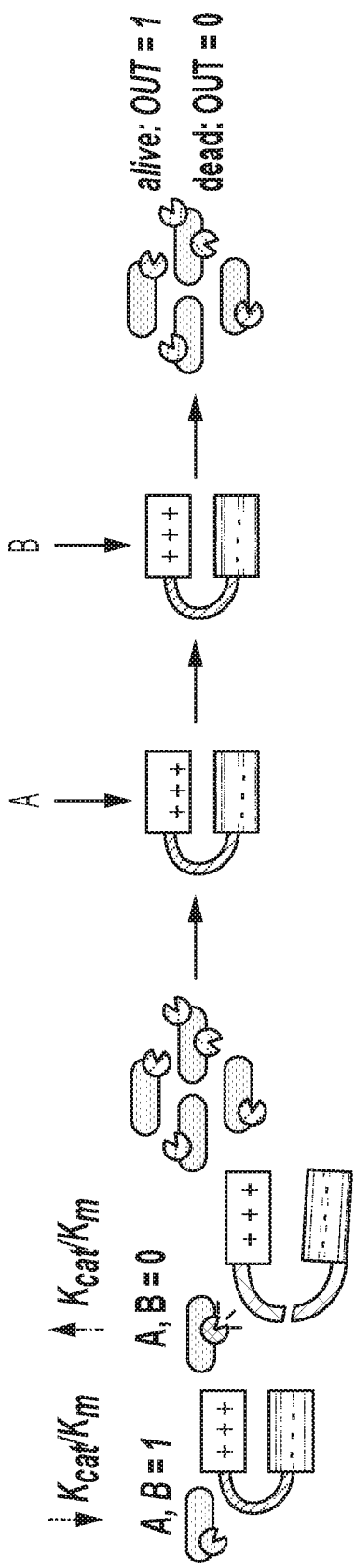
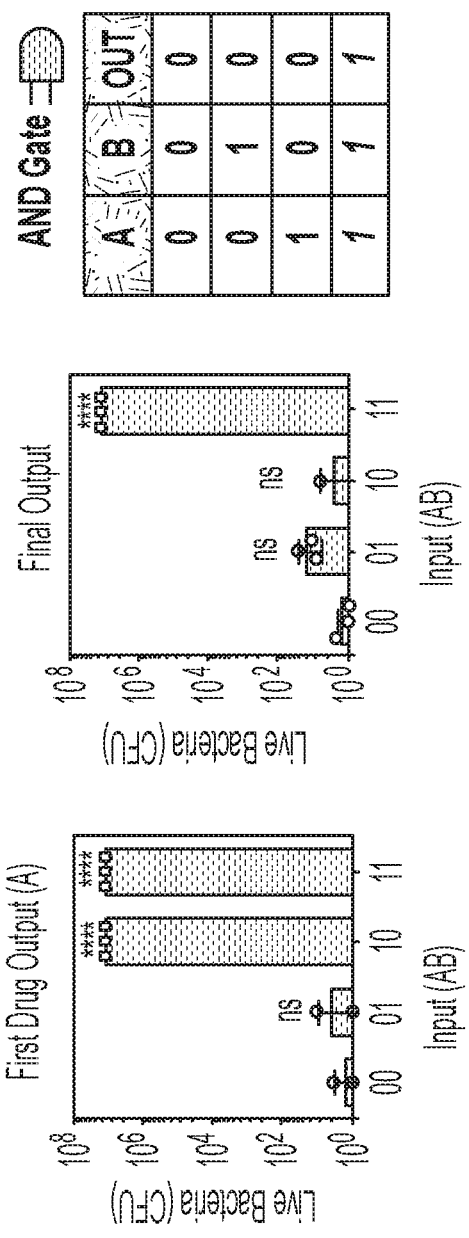
FIG. 9A
FIG. 9B
FIG. 9C
FIG. 9D

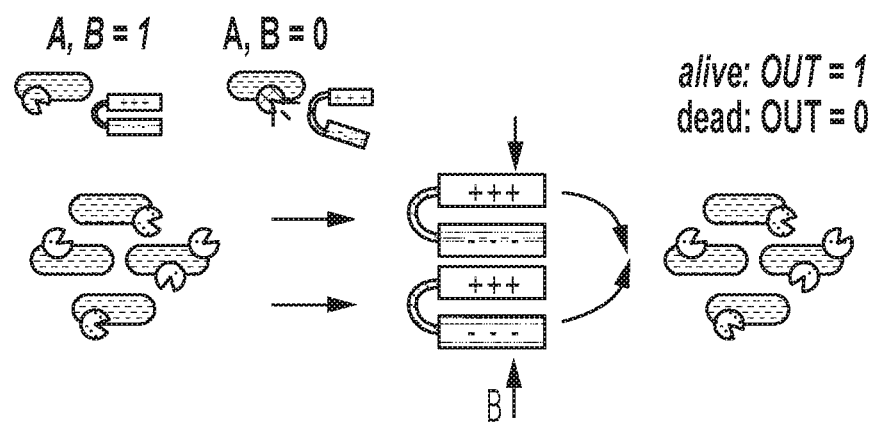
FIG. 9E
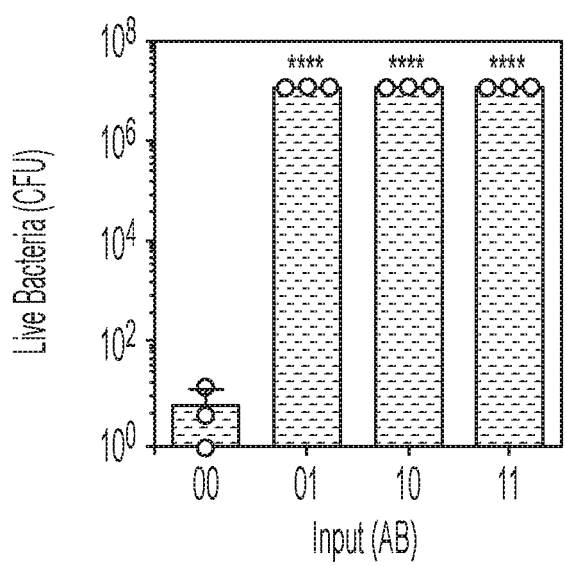
FIG. 9F
| A | B | OUT |
|---|---|-----|
| 0 | 0 | 0 |
| 0 | 1 | 1 |
| 1 | 0 | 1 |
| 1 | 1 | 1 |
FIG. 9G

SELF-TITRATING BACTERIAL PROTEASE-ACTIVATED PRODRUG

CROSS REFERENCE TO RELATED APPLICATIONS

This application is a national stage application, filed under 35 U.S.C. § 371, of International Patent Application No. PCT/US2019/051816 filed on Sep. 19, 2019, which claims benefit of and priority to U.S. Provisional Patent Application No. 62/733,347, filed on Sep. 19, 2018, which are incorporated herein by reference in their entirety.

TECHNICAL FIELD OF THE INVENTION

This invention is generally related to antimicrobial peptides and methods for treating bacterial infection.

REFERENCE TO SEQUENCE LISTING

The instant application contains a Sequence Listing which has been submitted electronically in ASCII format and is hereby incorporated by reference in its entirety. Said ASCII copy, created on Apr. 5, 2021, is named 064489_051US_(8010)_SL.txt and is 3,864 bytes in size.

BACKGROUND OF THE INVENTION

The rise of multidrug-resistant bacteria coupled with the lack of newly developed antibiotics has created a serious public health threat (Baquero, et al., *Current Opinion in Biotechnology*, 19:260-265 (2008); Gullberg, et al., *PLOS Pathogens*, 7:e1002158 (2011)). Understanding the causes of antibiotic failure improves the development of new drugs and informs clinical treatment strategies (Molina-Quioz, et al., *mBio*, 9: e02144-17 (2018); Cohen, et al., *Cell Host & Microbe*, 13:632-642 (2013); Allison, et al., *Nature*, 473:216 (2011)). These failure mechanisms are broadly classified into three distinct categories (i.e., resistance, persistence, and tolerance), which are characterized by the change in drug concentration and exposure time required to kill bacteria (Brauner, et al., *Nature Reviews Microbiology*, 14:320 (2016)). For example, resistance is characterized by genetic mutations which result in bacteria requiring significantly higher concentrations of antibiotic (minimum inhibitory concentration, MIC) to be lethal. By contrast, bacteria exhibiting tolerance or persistence require increased drug exposure time (minimum duration for killing, MDK), with the latter exhibiting a biphasic killing profile. Further, bacteria populations become tolerant through environmental conditions or genetic mutations, whereas persistence is an actively maintained, non-heritable state exhibited by a subpopulation of bacteria. Discriminating between these survival strategies employed by bacteria is crucial for the development of new drugs and clinical treatment decisions (Brauner, et al., *Nature Reviews Microbiology*, 14:320 (2016)).

Antibiotic success is markedly improved by proper titration of drugs, as overdosing leads to off-target toxicity and underdosing increases the likelihood of pathogens developing resistance (Bielicki, et al., *BMJ*, 351:h5447 (2015); Bailey, et al., *J Pediatr Pharmacol Ther*, 20(4): 309-315 (2015)). However, optimal drug doses are difficult to achieve over the course of treatment because infection burden changes dynamically over time, creating a moving target (Bielicki, et al., *BMJ*, 351:h5447 (2015); Bailey, et al., *J Pediatr Pharmacol Ther*, 20(4): 309-315 (2015); Iizumi, et al., *Arch Med Res*, 48(8):727-734 (2017)). Prodrugs, which represent ~10% of all FDA-approved drugs in the last decade, are a promising solution because they are automatically titrated by a disease-related activation mechanism, increase bioavailability, and reduce the risk of off-target effects (Rautio, et al., *Nat Rev Drug Discov*, 17(8): 559-587 (2018)). For example, prodrugs such as ganciclovir (Al-Badr and Ajarim in "Profiles of Drug Substances, Excipients and Related Methodology, Vol. 43 (ed. H. G. Brittain) 1-208 (Academic Press, 2018)) and sultamicillin (Baltzer, et al., *J Antibiot (Tokyo)*, 33(10):1183-1192 (1980)) are administered as biologically inactive forms and are enzymatically or chemically activated, respectively. Cationic antimicrobial peptides (AMPs) act by disrupting bacterial membranes and inducing inflammatory responses (Mahlapuu, et al., *Front Cell Infect Microbiol*, 6:194 (2016)), but suffer from off-target toxicity and low stability in vivo (Wimley and Hristova, *J Membr Biol*, 239(1-2):27-34 (2011); Bradshaw, *BioDrugs*, 17(4):233-240 (2003)). Therefore, there is a need for antimicrobial drugs that can confer maximal microbial killing with low off-target toxicity and a low incidence of resistant bacteria.

It is an object of the invention to provide compositions and methods for treating bacterial infection in subjects in need thereof.

SUMMARY OF THE INVENTION

It has been discovered that although antimicrobial peptide (AMP) prodrugs eliminate a majority of bacteria, a bacterial population exists that is defiant to the prodrug by proliferating in the presence of active prodrug by consistently outpacing the prodrug at all stages of growth. Disclosed herein are bacterial protease-activated prodrug compositions and methods of their use for the treatment and prevention of bacterial infection. Also disclosed are methods of reducing or eliminating defiant bacterial populations.

An exemplary prodrug composition includes a cationic antimicrobial peptide conjugated to an anionic peptide with a protease-cleavable linker substrate, wherein the antimicrobial peptide is inactive while it is in conjugation with the anionic peptide. The protease-cleavable linker substrate can be a protease substrate for a bacterial protease. In some embodiment, the protease substrate is OmpT. The protease-cleavable linker substrate can have an amino acid sequence according to any one of SEQ ID NO:1-3. The anionic peptide can be polyglutamic acid.

In one embodiment, cleavage of the protease-cleavable linker substrate releases the cationic antimicrobial peptide from the anionic peptide. The released cationic antimicrobial peptide is the active form of the peptide. In some embodiments, the prodrug does not exert effects on the subject unless the protease-cleavable linker substrate is cleaved by a bacterial protease.

Also provided are methods for improving prodrug treatment including steps of identifying a dimensionless quantity of the prodrug to discriminate between successful treatment and unsuccessful treatment of a subject with the prodrug, wherein identifying the dimensionless quantity uses mathematical modeling to determine a metric threshold wherein the growth or survival of infectious agents in the presence of the prodrug outweighs the activity of the prodrugs; assigning a value to the prodrug by modeling the infectious agents' response to the prodrug, wherein prodrugs having a modeled value greater than the metric threshold are deemed unsuccessful and prodrugs having a modeled value less that the metric threshold are deemed successful, and administering the prodrug to the subject in need thereof if the prodrug has a modeled value less than the metric threshold. In one embodiment, identifying the dimensionless quantity of the prodrug further includes determining environmental and genetic conditions in which infectious agents are unresponsive to a prodrug composition. The prodrug can be an antibacterial prodrug and the subject can have a bacterial infection. In some embodiments, the mathematical modeling uses the equation $$BAH = \log_{10}\left(\frac{r}{k_{cat}}\right),$$

wherein r is the growth rate of the bacteria and $k_{cat}$ is the catalytic turnover rate of the prodrug.

Another embodiment provides a method of treating a subject in need thereof by identifying a dimensionless quantity of each prodrug of a plurality of prodrugs to discriminate between successful treatment and unsuccessful treatment of a subject with the prodrug, wherein identifying the dimensionless quantity includes using mathematical modeling to determine a metric threshold wherein the growth or survival of infectious agents in the presence of the prodrug outweighs the activity of the prodrugs; assigning a value to the prodrug by modeling the infectious agents' response to the prodrug, wherein prodrugs having a modeled value greater than the metric threshold are deemed unsuccessful and prodrugs having a modeled value less that the metric threshold are deemed successful, and selecting two or more prodrugs for administration to the subject wherein the two or more prodrugs have modeled values covering a range of values, and administering the two or more prodrugs to the subject such that there is increased infectious agent killing when the two or more prodrugs are administered in comparison to administration of a single prodrug. The prodrugs can be an antimicrobial peptide conjugated to a polymer by a cleavable bond or cleavable linker, wherein the antimicrobial peptide has little or no antimicrobial activity while conjugated to the polymer and has antimicrobial activity when not bound to the polymer. The amount of each prodrug composition administered to the subject can be from 0.1 mg to 2000 mg of the prodrug. In some embodiments, the subject has a bacterial infection caused by a bacterium selected from the group consisting of Escherichia coli, Streptococcus, Staphylococcus, Corynebacterium, Listeria, Bacillus, Clostridium, Salmonella enteritidis, Salmonella typhi, Shigella, Pseudomonas aeruginosa, Helicobater, Stenotrophomonas, Bdellovibrio, Legionella pneumophila, Vibrio cholera, Neisseria gonorrhoeae, Neisseria meningitidis, Moraxella catarrhalis, Haemophilis influenza, Chlamydia trachomatis, Yersinia pestis, Klebsiella pneumoniae, Proteus mirabilis, Enterobacter cloacae, Serratia marcescens and Acinetobacter baumannii.

One embodiment provides a method of treating bacterial infection in a subject in need thereof by administering to the subject a plurality of prodrug compositions, wherein each prodrug composition is effective at killing bacteria across a different range of environmental or genetic factors. The range of environmental and genetic factors is defined as Bacterial Advantage Heuristic (BAH) and is calculated using the equation, $$BAH = \log_{10}\left(\frac{r}{k_{cat}}\right),$$

wherein r is the growth rate of the bacteria and $k_{cat}$ is the linker substrate catalytic turnover rate. Each prodrug kills bacteria under different environmental conditions such that bacteria that escape killing by one prodrug are killed by a secondary prodrug. The prodrug can include an antimicrobial peptide conjugated to a polymer by a protease-cleavable bond or protease-cleavable linker, wherein the antimicrobial peptide has little or no antimicrobial activity while conjugated to the polymer and has antimicrobial activity when not bound to the polymer.

BRIEF DESCRIPTION OF THE DRAWINGS

(FIG. 1F) against fluorescence-quenched linker substrates. Negative control samples contain the inhibitor aprotinin or linker substrate only. Shaded regions represent standard deviation. FIG. 1I is a graph showing results of a bacteria viability assay quantifying drug toxicity in various conditions (AMP, TEV protease, or locked AMP only, aprotinin+locked AMP, locked AMP negative control, relative to untreated bacteria control. FIGS. 1J-1M show immunofluorescent staining of the bacteria viability with untreated bacteria control (1J), aprotinin—locked AMP negative control (1K), AMP (1L), and TEV protease + unlocked AMP (1M).

FIGS. 3B-3J are graphs validating the model with serial CFU measurements (red and blue dots; n=3, error bars SEM) and ODE model simulations of nine conditions given extracted growth rate and enzyme kinetics parameter values.

FIG. 5A is a schematic of the model used to quantify r and $k_{cat}$ from bacterial cleavage assays. FIG. 5B-5J are graphs showing bacterial cleavage assays, from which growth rate (r) and enzyme kinetics ($k_{cat}/K_m$) are extracted, and BAH is calculated. Dotted line represents model after parameter fitting.

FIGS. 9A-9D show a bacterial viability assay validating the function of a prodrug-based AND gate. FIG. 9A is a schematic depicting two prodrug transistors arranged in series. FIGS. 9B-9C are graphs showing bacteria viability in the presence of various combinations of two substrates. FIG. 9D is a truth table showing results from FIGS. 9B-9C. FIGS. 9E-9G show a bacterial viability assay validating the function of a prodrug-based OR gate. FIG. 9E is a schematic depicting two prodrug transistors arranged in parallel. For AND and OR, input values were controlled with substrate sequence, where the substrate with high $k_{cat}/K_m$ corresponds to BAH=0 and the substrate with low $k_{cat}/K_m$ corresponds to BAH=1. FIG. 9F is a graph showing results of the bacterial viability assay and FIG. 9G is a truth table. Statistical comparisons are made with 00 condition. FIG. 9H is a schematic depicting heat-triggered liposome (black circle) loaded with drug (black squares=ampicillin). BAH=0 corresponds to temperature of 30° C. and BAH=1 corresponds to 37° C. FIG. 9I is a graph showing the results of the bacterial viability assay. FIG. 9H is a truth table. All truth tables depict ideal binary input-output combinations.

DETAILED DESCRIPTION OF THE INVENTION

Figures 1A, 1B, 1C:
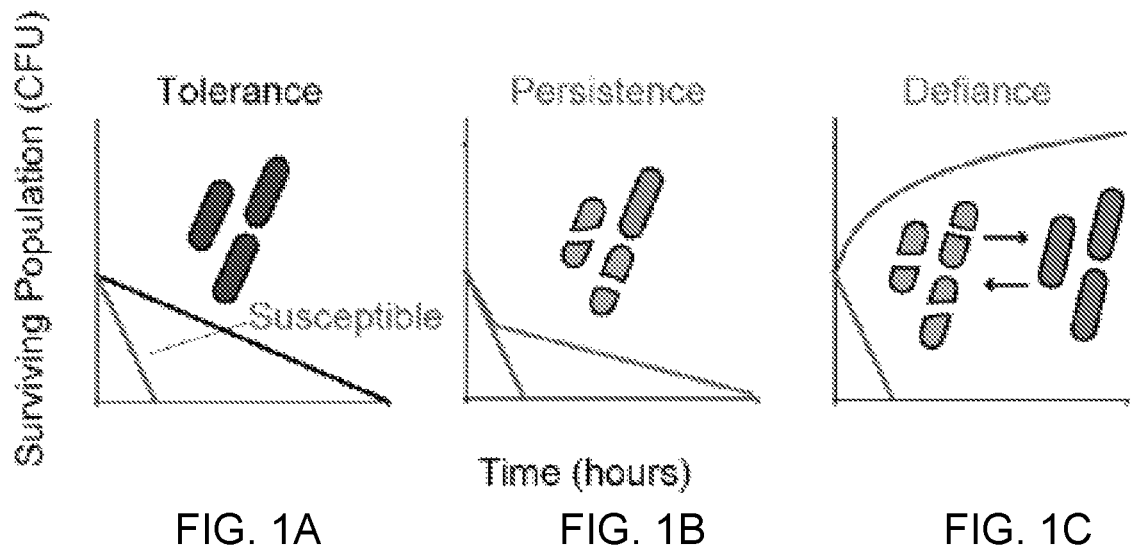
FIGS. 1A-1C are schematic illustrations comparing time-dependent killing profiles of bacteria exhibiting tolerance (FIG. 1A), persistence (FIG. 1B), or defiance (FIG. 1C).

It should be appreciated that this disclosure is not limited to the compositions and methods described herein as well as the experimental conditions described, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the terms "treat," "treating," "treatment" and "therapeutic use" refer to the elimination, reduction or amelioration of one or more symptoms of a disease or disorder. As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, a "prodrug" is a biologically inactive compound which can be metabolized in the body to produce a drug.

As used herein, "antimicrobial peptide" or "AMP", refers to a diverse class of naturally occurring molecules that are produced as a first line of defense by all multicellular organisms. These proteins can have broad activity to directly kill bacteria, yeasts, fungi, viruses and even cancer cells. In higher eukaryotic organisms, AMPS can also be referred to as 'host defense peptides', emphasizing their additional immunomodulatory activities. These activities are diverse, specific to the type of AMP, and include a variety of cytokine and growth factor-like effects that are relevant to normal immune homeostasis.

As used herein, a bacteria is "resistant" to a treatment modality when it no longer responds to a treatment or dose of a treatment that previously showed efficacy against the bacteria.

As used herein, "persistence bacteria" or "bacterial persistence" refer to a phenotype in which a subpopulation of bacteria exhibit slow growth coupled with an ability to survive antibiotic or antimicrobial treatment.

As used herein, "tolerant bacteria" or "bacterial tolerance" refer to a phenotype in which a population of bacteria can outlive exposure to increasing concentrations of an antibiotic by slowing down essential bacterial processes.

As defined herein, an "infectious agent" is an organism (typically a microorganism) that infiltrates and causes disease in another organism. Examples of infectious agents include but are not limited to viruses, bacteria, fungi, amoeba, and parasites.

II. Bacterial Protease-Activated Prodrugs

It has been discovered that although AMP prodrugs eliminate a majority of bacteria when contacted with the bacteria, a bacterial population exists that is defiant to the prodrug by proliferating in the presence of active prodrug by consistently outpacing the prodrug at all stages of growth. Disclosed herein are bacterial protease-activated prodrug compositions and methods of their use for the treatment and prevention of bacterial infection. An exemplary composition includes an antimicrobial peptide prodrug that is activated by bacterial proteases. In one embodiment, an antimicrobial peptide prodrug includes an antimicrobial peptide conjugated to a polymer by a cleavable linker. An exemplary peptide prodrug includes a cationic antimicrobial peptide conjugated to an anionic peptide via a protease-cleavable linker substrate such that the AMP is locked by charge complexation with the anionic peptides. Upon proteolytic cleavage of the linker, the hairpin prodrug is unlocked to release free AMP, creating a mechanism for auto-titration. In such an embodiment, increasing concentrations of bacteria activate higher concentrations of free drug. In the absence of bacteria, the prodrugs remain inactive and inert, and lack cytotoxic activity. Therefore, the prodrugs are only activated by bacteria and the amount of prodrug that is activated is proportional to the amount of bacteria present in the sample or the subject receiving the prodrug.

A. Antimicrobial Peptide

In one embodiment, the disclosed bacterial protease-activated prodrugs include an antimicrobial peptide conjugated to a polymer via a cleavable linker. In one embodiment, the antimicrobial peptide is a cationic antimicrobial peptide. Cationic antimicrobial peptides (AMPs) are a large group of low molecular weight natural peptides that play a role in innate immunity of most living organisms. Cationic AMPs are typically between about 10 to about 50 amino acid residues in length. In one embodiment, the cationic AMP is about 10, 12, 14, 16, 18, 20, 22, 24, 26, 28, 30, 32, 34, 36, 38, 40, 42, 44, 46, 48, or 50 amino acids in length. In one embodiment, the cationic AMPs have an overall positive charge. More than 2,400 cationic AMPs have been identified in various species ranging from insects to plants and animals. Cationic AMPs have a broad spectrum of activity, including rapid action against both Gram-positive and Gram-negative bacteria, fungi, viruses, and parasites. They act directly on bacteria by disrupting the plasma membrane or acting on specific intracellular targets to inhibit DNA, RNA, or protein synthesis processes, to inactivate essential intracellular enzymes, or to disrupt the plasma membrane formation and cell wall synthesis. AMPs exhibit a net positive charge and a high ratio of hydrophobic amino acids, allowing them to selectively bind to negatively charged bacterial membranes. Binding of AMPs to the bacterial membrane leads to non-enzymatic disruption.

Exemplary cationic AMPs include but are not limited to ambicin (nisin), subtilin, gallidermin, plectasin, mersacidin, vancomycin, bacitracin, SP1-1, MP196, SMAP-29, daptomycin, indolicin, cecropin A, protegrin (PG-1), defensin, thrombociding, β-defensin, polymixin B, gramicidin S, cathelicidin, cecropin(1-7)-melittin A(2-9) amide, and magainin-II. In one embodiment, the cationic AMP has the amino acid sequence (KLAKLAK)₂ (SEQ ID NO:4)

In some embodiments, the AMPs can be modified to increase their stability or their ability to effectively disrupt bacteria. Such modifications include but are not limited to covalent modification such as the removal or addition of covalent bonds, alterations in the amino acid sequence of the AMPs, amidation, and the addition of unnatural amino acids.

B. Anionic Peptide

In one embodiment, the disclosed bacterial protease-activated prodrugs include a polymer in conjugation with the cationic AMP such that the AMP is inactive while it is bound to the polymer. In some embodiments, the polymer is an anionic peptide with an overall negative charge, thus allowing it to lock in charge complexation with the positively charged AMP such that it maintains the AMP in an inactive state. In such an inactive state, the AMP cannot affect the subject nor can it have any effect on bacteria. The anionic peptide must lock with the cationic AMP in order to maintain its inactive state. Therefore, the anionic peptide and the cationic AMP should be paired such that they will complex together. In such an embodiment, the anionic peptide should be about the same length as the cationic AMP. In some embodiments, the anionic peptide is from about 10 to about 50 amino acid residues in length. In one embodiment, the anionic peptide is about 10, 12, 14, 16, 18, 20, 22, 24, 26, 28, 30, 32, 34, 36, 38, 40, 42, 44, 46, 48, or 50 amino acids in length. In one embodiment, the anionic peptide is polyglutamic acid. In other embodiments, the anionic peptide is polyaspartic acid. The amino acids can be in the natural L-configuration or they can be in the unnatural D-configuration.

C. Protease-Cleavable Linker Substrate

The disclosed bacterial protease-activated prodrugs include a cleavable linker conjugating the cationic AMP to the polymer. In one embodiment, the cleavable linker is a protease-cleavable linker substrate that maintains the cationic AMP in a locked conformation by charge complexation with the anionic peptides. Upon cleavage by the protease, the cationic AMP is released from the anionic peptide and can act upon bacteria. In one embodiment, the protease is specific to the bacteria that are present in the sample or the subject. In such an embodiment, the bacteria act as an auto-titrating mechanism wherein the AMP is released from the peptide only when there is bacteria present.

In one embodiment, the protease-cleavable linker substrate is a bacterial protease substrate. Exemplary bacterial protease substrates include but are not limited to those that are cleaved by *E coli* proteases such as OmpT, OmpP, ElaD, heat shock protein 31, putative Cys protease YhbO, DegP, DegQ, and DegS, *Yersinia pestis* Pla, *Salmonella enterica* PgtE, and *Shigella flexneri* SopA. In one embodiment, the protease is OmpT. Outer membrane protease T (OmpT) is a membrane-bound bacterial protein that is widely conserved across gram-negative bacteria of the Enterobacteriaceae family and recognizes a variety of targets that contribute to its virulence (e.g., plasminogen).

In one embodiment, the bacterial protease has one of the following amino acid sequences:

```
                                    (SEQ ID NO: 6)
AAF, GGL, LLE, AFK, QAR, VPR, PFR, AAN, GAM, IIW,

VLK, GGR, CKR, LLVY, (SEQ ID NO: 7)
RLRGG, (SEQ ID NO: 8)
AAPV, (SEQ ID NO: 9)
DVED, (SEQ ID NO: 10)
GPLGP,
or
                                    (SEQ ID NO: 11)
DEFIADCE.
```

In one embodiment, the protease-cleavable linker substrate has the amino acid sequence

```
                                    (SEQ ID NO: 1)
            RRSRRV, (SEQ ID NO: 2)
            RKTRR, (SEQ ID NO: 5)
            NLYFQG,
            or
                                    (SEQ ID NO: 12)
            KPLGMWSR.
```

Other exemplary linkers that are contemplated include but are not limited to PEG linkers, hydrazone and hydrazide linker moieties, disulfide linkers, β-glucuronide linkers, and acid-labile linkers.

D. Pharmaceutical Compositions

Pharmaceutical compositions including the disclosed bacterial protease-activated prodrugs are provided. Pharmaceutical compositions containing the prodrugs can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

For the disclosed prodrugs, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For the disclosed prodrugs, generally dosage levels of 0.1 to 1000 mg per dose are administered to mammals. The prodrugs can be administered to the subject once daily, twice daily, three times daily, or four times daily. Generally, for intravenous injection or infusion, dosage may be lower.

In certain embodiments, the prodrug is administered locally, for example by injection directly into a site to be treated. Typically, the injection causes an increased localized concentration of the prodrug composition which is greater than that which can be achieved by systemic administration. The prodrug compositions can be combined with a matrix as described above to assist in creating an increased localized concentration of the polypeptide compositions by reducing the passive diffusion of the polypeptides out of the site to be treated.

1. Formulations for Parenteral Administration

In some embodiments, compositions disclosed herein are administered in an aqueous solution, by parenteral injection. The formulation may also be in the form of a suspension or emulsion. In general, pharmaceutical compositions are provided including effective amounts of a prodrug, and optionally include pharmaceutically acceptable diluents, preservatives, solubilizers, emulsifiers, adjuvants and/or carriers. Such compositions optionally include one or more of the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Oral Administration

In embodiments the compositions are formulated for oral delivery. Oral solid dosage forms are described generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the disclosed. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder (e.g., lyophilized) form. Liposomal or proteinoid encapsulation may be used to formulate the compositions. Liposomal encapsulation may be used and the liposomes may be derivatized with various polymers (e.g., U.S. Pat. No. 5,013,556). See also Marshall, K. In: Modern Pharmaceutics Edited by G. S. Banker and C. T. Rhodes Chapter 10, 1979. In general, the formulation will include the peptide (or chemically modified forms thereof) and inert ingredients which protect peptide in the stomach environment, and release of the biologically active material in the intestine.

The agents can be chemically modified so that oral delivery of the derivative is efficacious. Generally, the chemical modification contemplated is the attachment of at least one moiety to the component molecule itself, where the moiety permits uptake into the blood stream from the stomach or intestine, or uptake directly into the intestinal mucosa. Also desired is the increase in overall stability of the component or components and increase in circulation time in the body. PEGylation is an exemplary chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) *J. Appl. Biochem.* 4:185-189].

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. The agent can be incorporated into an inert matrix which permits release by either diffusion or leaching mechanisms, e.g., gums. Slowly degenerating matrices may also be incorporated into the formulation. Another form of a controlled release is based on the Oros therapeutic system (Alza Corp.), i.e., the drug is enclosed in a semipermeable membrane which allows water to enter and push drug out through a single small opening due to osmotic effects.

For oral formulations, the location of release may be the stomach, the small intestine (the duodenum, the jejunum, or the ileum), or the large intestine. In some embodiments, the release will avoid the deleterious effects of the stomach environment, either by protection of the agent (or derivative) or by release of the agent (or derivative) beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D™, Aquateric™, cellulose acetate phthalate (CAP), Eudragit L™, Eudragit S™, and Shellac™. These coatings may be used as mixed films.

III. Prodrug Biological Circuits

Disclosed herein are methods of predicting whether bacteria will become defiant to the disclosed bacterial protease-activated prodrug compositions to aid in the development of potent bacterial protease-activated prodrugs. As used herein, "defiant bacteria" or "bacterial defiance" refer to a phenotype in which a subpopulation of bacteria proliferate in the presence of an active prodrug by consistently outpacing the drug activation at all stages of growth. Also disclosed are biological circuits to combat prodrug failure due to defiance.

In one embodiment, a system of coupled ordinary differential equations (ODE) that model the dynamics of the bacteria-prodrug competition can be used to identify a dimensionless quantity—the Bacterial Advantage Heuristic (B.A.H.)—which predicts with accuracy whether bacteria will become defiant under a broad range of environmental conditions. B.A.H. is a universal, dimensionless quantity that can be calculated for each unique prodrug that is manufactured. The B.A.H. can aide in combating prodrug defiance and can be used to create prodrug biological circuits which will be discussed in detail below.

In one embodiment, the competing balance between growth rate and enzymatic turnover defines the Bacterial Advantage Heuristic (B.A.H.) and is represented by Equation 1.2.

$$BAH = \log_{10}\left(\frac{r}{k_{cat}}\right) \qquad \text{(Equation 1.2)}$$

This quantity reflects that bacteria have a higher probability of switching to the defiance phenotype under conditions that promote a faster growth rate, r, and slower enzymatic activity, $k_{cat}$. In one embodiment, for any environmental or genetic condition that produces a $BAH > BAH_{crit}$, the bacteria will survive the prodrug treatment, and for $BAH < BAH_{crit}$, the bacteria will die.

In one embodiment, $BAH_{crit}$ is calculated for each prodrug composition that is produced such that a range of efficacy is known across a range of environmental and genetic conditions for each prodrug. Having the ranges of efficacy allows for the selection of prodrug compositions to meet individual needs for subjects receiving the prodrug treatment. In another embodiment, the $BAH_{crit}$ values can be used to personalize a multi-drug combination treatment.

One embodiment provides biological circuits to combat prodrug failure due to defiance that eliminate bacteria under all conditions (BAH values) by recognizing that AMP prodrugs behave analogously to transistors. Above a critical BAH threshold, bacteria begin proliferating in the presence of active prodrug by consistently outpacing the prodrug at all stages of growth and exhibit defiance. In one embodiment, to combat bacterial defiance, a multi-prodrug approach can be used to eliminate defiant bacteria that would otherwise resist treatment to a single prodrug.

Combinations of prodrugs and other therapeutics can be administered to a subject in order to ensure all bacteria are cleared even when they exhibit a defiant phenotype. In one embodiment, a plurality of bacterial protease-activated prodrugs having a range of $BAH_{crit}$ values can be administered to a subject in order to kill bacteria even if they reach the threshold of defiance. For example, a combination of prodrug A and prodrug B can be administered to a subject. Prodrug A has a $BAH_{crit}$ of 1, therefore in environmental or genetic conditions in which the B.A.H. exceeds 1 the prodrug will no longer be effective at killing bacteria. In such a situation, prodrug B, having a $BAH_{crit}$ of 5 will kill bacteria in conditions in which the B.A.H. exceeds 1. In another embodiment, other means such as heat-triggered, drug-loaded liposomes can be used to overcome the defiant bacterial populations once they reach the threshold for defiance for all bacterial prodrugs that have been administered.

In one embodiment, the disclosed bacterial protease-activated prodrugs can be engineered to have specific B.A.H. values by altering properties such as pharmacokinetic properties (activation rate and $k_{cat}$), environmental properties (survival rate in specific temperatures or lack of nutrients), decay constant (biological half-life), and catalytic efficiency.

IV. Methods of Treating Bacterial Infection

Disclosed herein are compositions and methods for treating disease caused by infectious agents in a subject in need thereof. In one embodiment, an effective amount of at least one of the disclosed bacterial protease-activated prodrugs is administered to a subject in need thereof. In another embodiment, the subject is administered a plurality of different bacterial protease-activated prodrugs. The subject can have a bacterial infection, or can be suspected of having a bacterial infection. In other embodiments, the subject has a viral infection, a fungal infection, an amoeba infection, or a parasitic infection.

One embodiment provides a method of treating a subject in need thereof by (a) identifying a dimensionless quantity of each prodrug of a plurality of prodrugs to discriminate between successful treatment and unsuccessful treatment of a subject with the prodrug, wherein identifying the dimensionless quantity uses mathematical modeling to determine a metric threshold wherein the growth or survival of cells in the presence of the prodrug outweighs the activity of the prodrugs, (b) assigning a value to the prodrug by modeling the diseased cell response to the prodrug, wherein prodrugs having a modeled value greater than the metric threshold are deemed unsuccessful and prodrugs having a modeled value less that the metric threshold are deemed successful, (c) selecting two or more prodrugs for administration to the subject wherein the two or more prodrugs have modeled values covering a range of values, and (d) administering the two or more prodrugs to the subject such that there is increased diseased cell killing when the two or more prodrugs are administered in comparison to administration of a single prodrug.

The infected subject is administered an effective amount of the bacterial protease-activated prodrug to reduce or eliminate bacteria at the site of infection. In one embodiment, an effective amount of the bacterial protease-activated prodrug is calculated based upon several factors including the subject's weight, the bacterial load detected within the subject, other therapeutic agents that the subject has taken for the infection, and other factors as necessary. In general, the prodrugs are typically administered at a dose of 0.1 mg to 2000 mg of the prodrug.

In one embodiment, the infected subject is administered the bacterial protease-activated prodrug once daily, twice daily, three times daily, or four times daily. In another embodiment, the infected subject is administered the bacterial protease-activated prodrug for one week, two weeks, three week, or more than three weeks. The infected subject is typically administered the disclosed bacterial protease-activated prodrugs at least until tests show that no more bacteria is present in a biological sample obtained from the subject. The biological sample can be blood, saliva, urine, skin or stool.

Also provided is a method for improving prodrug treatment by (a) identifying a dimensionless quantity of the prodrug to discriminate between successful treatment and unsuccessful treatment of a subject with the prodrug, wherein identifying the dimensionless quantity comprises using mathematical modeling to determine a metric threshold wherein the growth or survival of cells in the presence of the prodrug outweighs the activity of the prodrugs, (b) assigning a value to the prodrug by modeling the diseased cell response to the prodrug, wherein prodrugs having a modeled value greater than the metric threshold are deemed unsuccessful and prodrugs having a modeled value less that the metric threshold are deemed successful, and (c) selecting the prodrug for administration to a subject in need thereof if the prodrug has a modeled value less than the metric threshold. Identifying the dimensionless quantity of the prodrug further comprises determining environmental and genetic conditions in which diseased cells are unresponsive to a prodrug composition. The mathematical modeling uses the equation $$BAH = \log_{10}\left(\frac{r}{k_{cat}}\right),$$

wherein r is the growth rate of the bacteria and $k_{cat}$ is the catalytic turnover rate of the prodrug.

A. Subjects to be Treated

The disclosed bacterial protease-activated prodrugs treat and reduce the number of bacteria in a subject in need thereof. In one embodiment, the bacterial protease-activated prodrugs reduce symptoms associated with bacterial infection.

In one embodiment, the bacterial infection is cause by a Gram-positive bacteria. Exemplary Gram-positive bacteria include but are not limited to bacteria from the genera *Streptococcus*, *Staphylococcus*, *Corynebacterium*, *Listeria*, *Bacillus*, and *Clostridium*.

In another embodiment, the bacterial infection is caused by a Gram-negative bacteria. Exemplary Gram-negative bacteria include but are not limited to *Escherichia coli*, *Salmonella* such as *Salmonella enteritidis* and *Salmonella typhi*, *Shigella*, *Pseudomonas* such as *Pseudomonas aeruginosa*, *Helicobater*, *Stenotrophomonas*, *Bdellovibrio*, *Legionella pneumophila*, *Vibrio cholera*, *Neisseria* such as *Neisseria gonorrhoeae* and *Neisseria meningitidis*, *Moraxella catarrhalis*, *Haemophilis influenza*, *Chlamydia trachomatis*, *Yersinia pestis*, *Klebsiella pneumoniae*, *Proteus mirabilis*, *Enterobacter cloacae*, *Serratia marcescens* and *Acinetobacter baumannii*.

Bacteria cause a wide-range of diseases based on the bacteria and anatomical location of the infection. Common diseases caused by bacterial infection include but are not limited to foodborne illness (*E. coli*), respiratory diseases (*Pseudomonas aeruginosa*, *Klebsiella pneumoniae*, *Moraxella catarrhalis*, *Haemophilis influenza*, *Legionella pneumophila*), sexually-transmitted diseases (*Neisseria gonorrhoeae*, *Chylamidia trachomatis*), meningitis (*Neisseria meningitidis*), urinary problems (*Escherichia coli*, *Proteus mirabilis*, *Enterobacter cloacae*, *Serratia marcescens*), gastrointestinal problems (*Helicobacter pylori*, *Salmonella enteritidis*, *Salmonella typhi*), and the plague (*Yersinia pestis*). In one embodiment, the disclosed bacterial protease-activated prodrugs are administered to a subject infected with bacteria to kill the bacteria and reduce symptoms of diseases associated with the bacterial infection.

EXAMPLES

Example 1. A Bacteria-Activatable Prodrug Targets *E. coli* Protease OmpT

Materials and Methods:

Protease Cleavage Assays: All protease cleavage assays were performed with a BioTek Cytation 5 Imaging Plate Reader, taking fluorescent measurements at 485/528 nm (excitation/emission) for read-outs measuring peptide substrates terminated with FITC (Fluorescein isothiocyanate). Kinetic measurements were taken every minute over the course of 60-120 minutes at 37 C. Tobacco Etch Virus protease (TEVp), along with its substrate and buffer was obtained from Anaspec, Inc. (Fremont, Calif.). Activity RFU measurements were normalized to time 0 measurement, and as such represent fold change in signal. Outer Membrane Protease T (i.e., OmpT, Protease 7) was purchased from Lifespan Biosciences (Seattle, WA). OmpT fluorescent peptide substrate was custom ordered from Genscript (Piscataway, NJ).

Bacterial culture and cytotoxicity measurement: DH5a *Escherichia coli* were a gift from Todd Sulchek's BioMEMS lab at Georgia Tech. *E. coli* were cultured in LB broth (Lennox) at 37 C and plated on LB agar (Lennox) plates. LB broth was purchased from Millipore Sigma (Burlington, Mass.) and LB agar was purchased from Invitrogen (Carlsbad, Calif.). AMP and locked AMP were custom ordered from Genscript (Piscataway, NJ). See Table 1 for more information. Bacteria were grown to a concentration of $10^9$ CFU/mL before being used for experiments. Concentration was estimated by measuring the OD600 of the bacterial suspension, and assuming an OD600 of 1.000 corresponds to a concentration of $8 \times 10^8$ CFU/mL. Bacterial cell viability was measured by making eight 10-fold serial dilutions, and plating three 10 uL spots on an LB agar plate. Plates were incubated overnight at 37° C., and CFUs were counted. Untreated bacteria CFU counts served as control for 0% cytotoxicity, and bacteria+IPA (or 0 countable CFUs) served as control for 100% cytotoxicity.

TABLE 1

Linker Sequences.

| Name | Peptide Sequence | SEQ ID NO |
|---|---|---|
| Locked AMP (linker 1) | EEEEEEEEEEEEERRSRRVRRRRR RRRR | 13 |
| Locked AMP (linker 2) | EEEEEEEEEEERKTRRRRRRRRR | 14 |
| Locked AMP (linker 3) | EEEEEEEEENLYFQGRRRRRRRRR | 15 |
| Locked AMP Probe | DABCYL-EEEEEEEEEEEERRSR RVRRRRRRRRR[Lys(5-FAM)] | 16 |
| OmpT Probe | DABCYL-RRSRRV-Lys(5-FAM) | 17 |

Figure 1D:
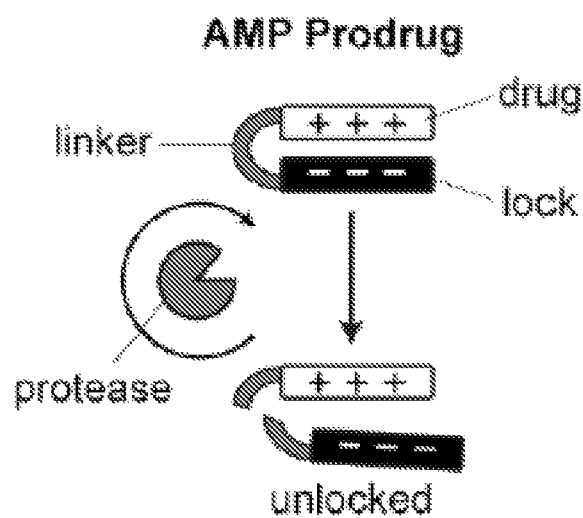
FIG. 1D is a schematic illustration of a cationic AMP drug locked by an anionic peptide lock with a protease-cleavable linker (image above arrow) that is activated by OmpT protease activity.
Figure 1E:
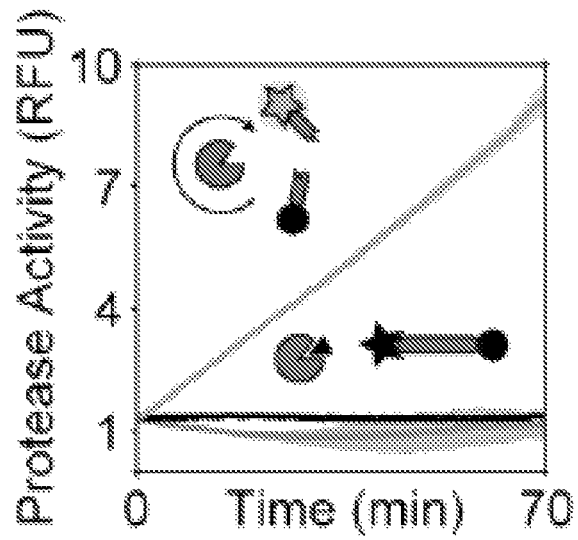
FIGS. 1E-1F are graphs showing the results of cleavage assays measuring the activity of recombinant OmpT protease (FIG. 1E) and OmpT expressed on the surface of E. coli.
Figure 1F:
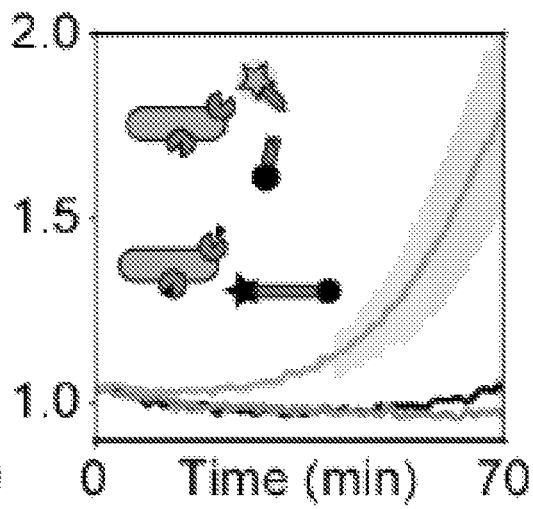
Figure 1G:
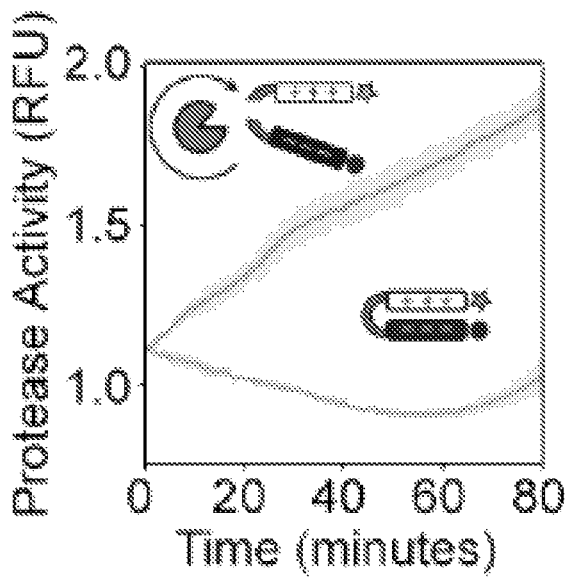
FIGS. 1G-1H are graphs showing the results of cleavage assays measuring the activity of recombinant OmpT (FIG. 1G) or OmpT expressed on the surface of E. coli (FIG. 1H) against fluorescently labeled hairpin prodrugs or hairpin prodrugs only control. Shading represents standard deviation (n=3). All cleavage assays plotted as fold change in RFU from initial time point.
Figure 1H:
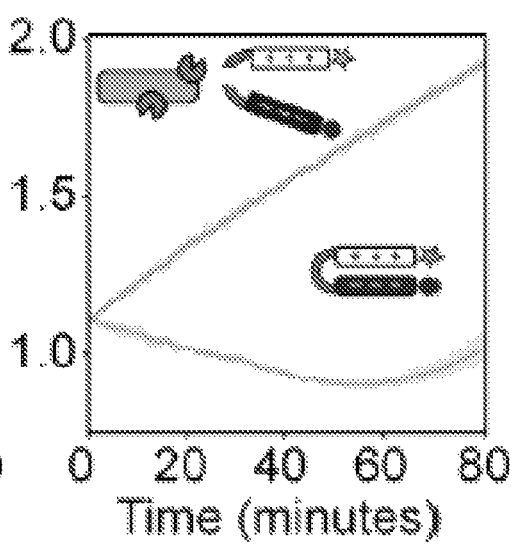
Figure 2A:
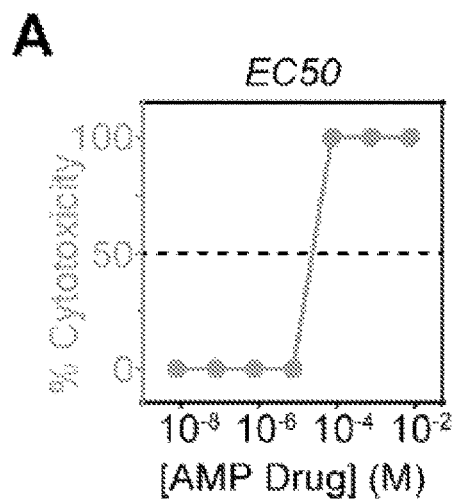
FIG. 2A is a graph showing EC50 measurement on a sample of E. coli exposed to increasing concentrations of AMP.
Figure 2B:
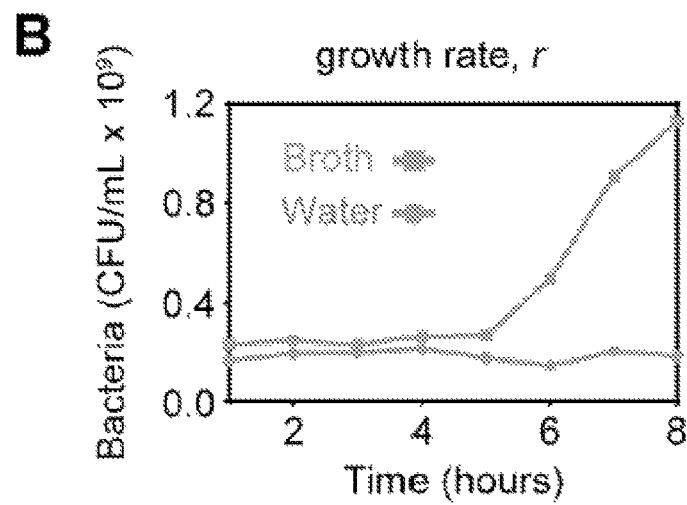
FIG. 2B is a graph showing growth rate calculation of E. coli in broth and water by measuring OD at 600 nm.
Figure 2C:
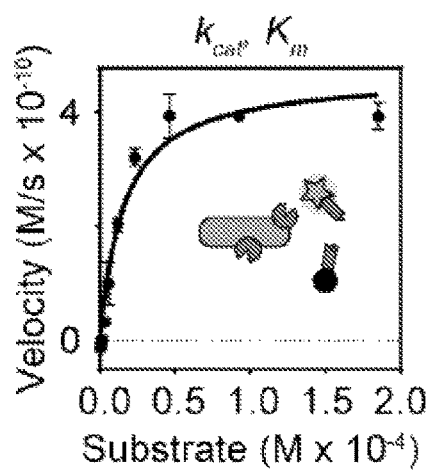
FIG. 2C is a graph showing cleavage velocity calculated by measuring $k_{cat}/K_m$ from a series of cleavage assays incubating E. coli at a range of substrate concentrations.
Figure 2D:
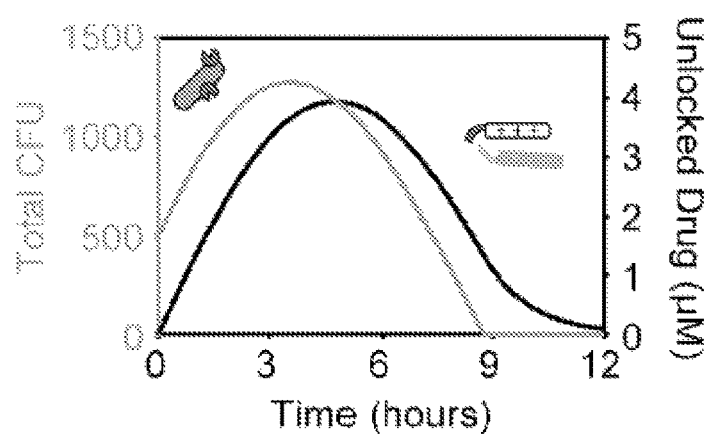
FIG. 2D is a graph showing the predicted dynamics of the bacteria and unlocked drug population given empirical parameter values. Error bars are standard deviation (n=3).

Results:

To construct bacteria-activated prodrugs, cationic (polyarginine) antimicrobial peptides (AMPs) in charge complexation with anionic peptide locks (polyglutamic acid) by a linker peptide (RRS|RRV) specific for the ubiquitous bacterial protease OmpT (Olson, et al., *Integrative Biology: Quantitative Biosciences from Nano to Macro*, 1: 382-393 (2009)) were synthesized. Upon proteolytic cleavage of the linker, the hairpin prodrug is unlocked to release free AMP, creating a mechanism for auto-titration (FIG. 1D). To demonstrate linker specificity for OmpT, an activity probe (McCarter, et al, *Journal of Bacteriology*, 170:1245-1253 (1988); Kwong, et al, *Nat Biotech*, 31:63-70 (2013); Holt, et al, *JoVE*, e57937 (2018); Mac, et al, *Nat Biomed Eng*, (2019); Zhuang, Q., et al, *bioRxiv*, 564906 (2019); Holt, et al, *Biomaterials Science*, 5: 463-474 (2017)) with free linker peptides containing a fluorophore-quencher pair was synthesized. OmpT activity was detected in samples incubated with recombinant OmpT or live *E. coli* culture. Conversely, no activity was observed in samples containing the serine protease inhibitor, Aprotinin, which inhibits OmpT when present in micromolar concentrations (Brannon, et al, *Infection and Immunity*, 83: 2300-2311 (2015)) (FIGS. 1E-1F). Similar cleavage activity was observed using this linker substrate when fully integrated into hairpin AMP drug-lock complexes, confirming that linker presentation within a constrained conformational state did not affect cleavage activity by OmpT (FIGS. 1G-1H). To measure cytotoxicity of unlocked drug, bacteria was dosed with free AMP. A significant reduction in colonies compared to untreated controls was observed (FIGS. 1I-1M). To confirm prodrug specificity, AMP drug-lock complexes were synthesized using linker peptides specific for OmpT or Tobacco Etch Virus Protease (TEV), which exhibits orthogonal protease specificity (Kapust, et al., *Protein Engineering, Design and Selection*, 14:993-1000 (2001). Elimination of bacteria was observed only in samples containing OmpT-specific AMP prodrugs or samples treated with both TEV and TEV-specific AMP prodrugs. All control samples containing either TEV-specific prodrug alone or Aprotinin inhibitor did not significantly reduce bacteria load (FIGS. 1I-1M, Table 1). These results showed that AMP drug-lock complexes are inert and lack cytotoxic activity until activation by protease activity.

Example 2. Kinetic Model of Prodrug Treatment Reveals a Binary Outcome

Figure 3A:
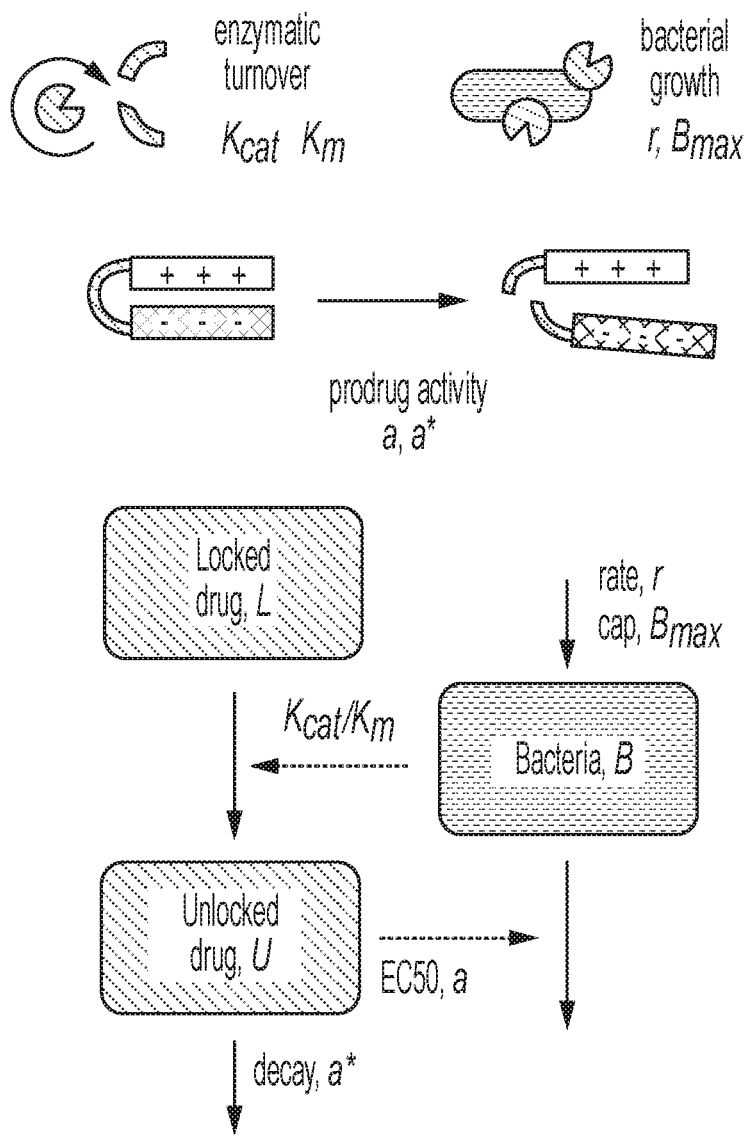
FIG. 3A is a graphical representation of the multi-rate model of bacteria (B), locked drug (L), and unlocked (U) drug populations. Legend describes the agents associated with each variable.
Figure 3K:
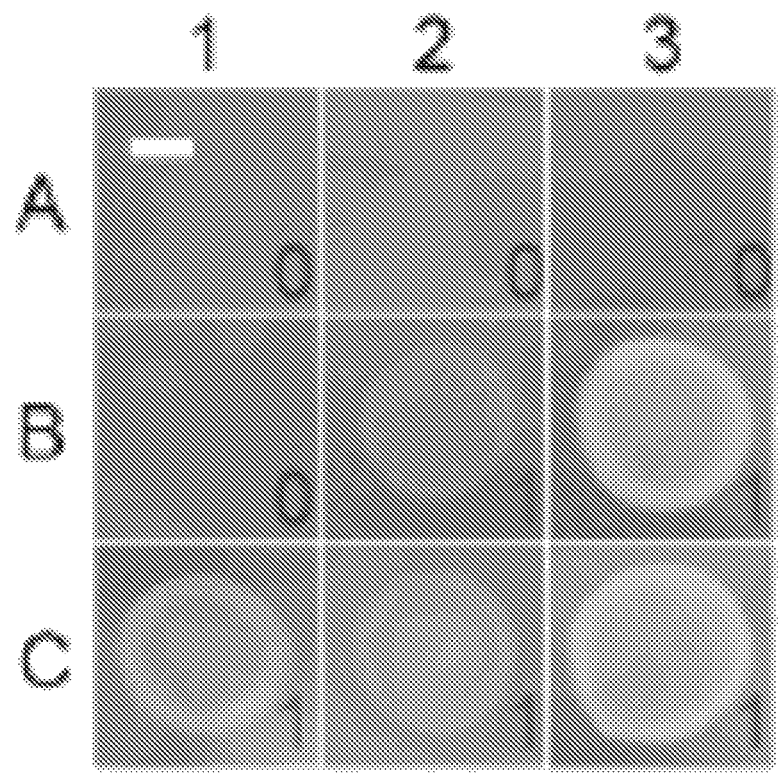
FIG. 3K is a photograph showing representative agar plates taken at end-point showing the binary presence (1) or absence (0) of bacterial growth for nine environmental conditions (A1-C3, scale bar=4 mm).
Figure 3L:
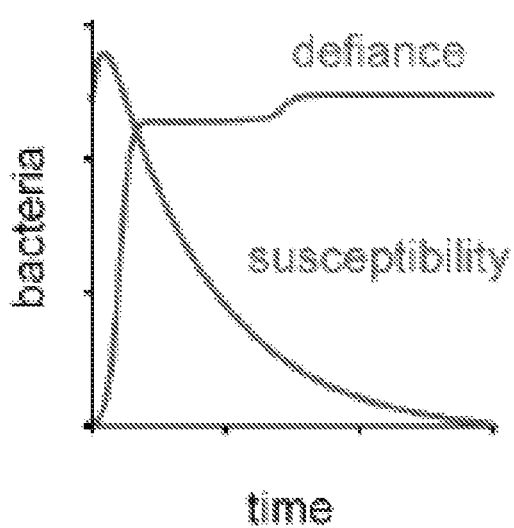
FIG. 3L is a schematic graph depicting that bacterial defiance is characterized by proliferation in the presence of activated drug.

Results:

To quantitatively understand how the rate of prodrug activation competes with the number of living bacteria, a mathematical model was built using a system of nonlinear ordinary differential equations (ODE). In said system, the three dynamic populations are the Bacteria, B, the Locked drug, L, and the Unlocked drug, U, for which governing ODEs were formulated by considering the system parameters that affect populational change over time. For this prodrug system, increased *E. coli* growth results in increased proteolytic activation of AMP, which in turn lyses bacteria to create a negative feedback loop. Therefore, the bacteria population B was modeled as increasing the rate of enzymatic drug conversion (i.e., L to U) and the unlocked drug population U as increasing the rate of bacterial death (FIG. 3A). To account for the fact that bacterial growth rate, r, slows down as environmental resources become limiting (i.e., carrying capacity, $B_{max}$), a logistic growth model was used (Fujikawa, et al., *Journal of Food Hygenic Society of Japan*, 44: 155-160 (2003)), which produces an S-shaped curve and has been used extensively in biology to study population expansion (Verhulst, P. F., *Nouveaux Mémoires de l'Académie Royale des Sciences et Belles-Lettres de Bruxelles* (1845)) and tumor growth (Atuegwu, et al., *Translational Oncology*, 6: 256-264 (2013)). By contrast, the rate of *E. coli* death is proportional to the concentration of unlocked drug, U, according to a proportionality constant, a, that represents the amount of AMP required to kill *E. coli* per unit time (Table 2, Equation 1.1).

$$\frac{dB}{dt} = rB\left[1 - \frac{B}{B_{max}}\right] - a^{-1}U \quad \text{(Equation 1.1)}$$

To model the rate of enzymatic activation of locked drugs, L, by OmpT, Michaelis-Menten (MM) kinetics were applied, where the rate of substrate activation is determined by the catalytic rate of the reaction, $k_{cat}$, and the half-maximal substrate concentration, $K_m$ (Equation 1.3). Here it was assumed the system constituted a well-mixed solution of freely diffusing substrates (i.e., locked drug) in large excess, which were valid assumptions for this study since AMP prodrug was present at concentrations ~102 micromolar in an aqueous environment. Because the total amount of drug is conserved, the MM activation rate of unlocked drug, U, was defined as opposite of the degradation rate of locked drug L (Equation 1.4). A term to account for the loss of active AMPS was included according to a proportionality constant, a*, that represents the number AMP required to kill one *E. coli*. This term was necessary as AMPS lyse *E. coli* by intercalating with bacterial membranes (Roversi, et al. *ACS Chemical Biology*, 9:2-3-2007 (2014)) and therefore are removed from the system and unable to target additional bacteria.

$$\frac{dL}{dt} = -k_{cat}B\frac{L}{K_m + L} \quad \text{(Equation 1.3)}$$

$$\frac{dU}{dt} = k_{cat}B\frac{L}{K_m + L} - a^*a^{-1}U \quad \text{(Equation 1.4)}$$

To fit this model to the disclosed system, the values for relevant parameters, including enzymatic efficiency (e.g., $k_{cat}$, $K_m$), bacterial growth (e.g., r, $B_{max}$), and prodrug activity (e.g., a, a*) were measured (FIGS. 2A-2D, Table 2). This allowed for the prediction of bacteria-prodrug response curves (FIGS. 3B-3J) across nine distinct combinations of $k_{cat}$ and r values, which were experimentally controlled by altering the ambient temperature and concentration of broth (conditions labeled A1-3, B1-3, and C1-3). Strikingly, the model anticipated a binary bacterial response to prodrug treatment that would be evident within 24 hours; bacteria were predicted to be either susceptible to the prodrug and die or to exhibit a drug-invariant phenotype and proliferate to saturating levels (FIGS. 3B-3L). To experimentally validate the model predictions, bacteria were incubated with prodrugs under the defined nine conditions, and the number of living bacteria were quantified longitudinally over the course of a 24 hour treatment window. Quantified bacterial counts taken during the course of treatment as well as at endpoint closely matched the values predicted by the model (R2=0.84; FIGS. 3B-3L) and likewise revealed a binary bacterial response to prodrugs leading to antibiotic failure. This form of resistance to prodrugs was defined as bacterial "defiance." Collectively, these experiments demonstrate that when *E. coli* are exposed to the AMP prodrug, the model can be used to predict bacterial growth kinetics, which ultimately result in a binary outcome.

TABLE 2

Bacterial parameter measured.

| Variable | Value | Units | Notes |
|---|---|---|---|
| r | 0.1-3 | $h^{-1}$ | Bacterial growth rate |
| kcat | 0.7-25e10 | $h^{-1}$ | Enzyme catalytic turnover |
| Km | 9e12 | $\mu L^{-1}$ | Michaelis constant |
| Bmax | 1000 | $\mu L^{-1}$ | Max bacteria concentration in tube |

TABLE 2-continued

Bacterial parameter measured.

| Variable | Value | Units | Notes |
|---|---|---|---|
| a | 1e11 | $h^{-1}$, AMP/bacteria/hr | Cytotoxic efficiency, EC50 |
| a* | 2.4e11 | AMP/bacteria | AMP decay |

TABLE 3

| Location (row, column) | Temperature, °C. | LB Broth Concentration | $r$ ($h^{-1}$) | $k_{cat}$ ($h^{-1}$) × $10^{10}$ |
|---|---|---|---|---|
| A1 | 37 | 0% | 0.1 | 25 |
| A2 | 30 | 2% | 0.14 | 13.6 |
| A3 | 37 | 2% | 0.3 | 22 |
| B1 | 37 | 4% | 0.5 | 15 |
| B2 | 37 | 6% | 0.85 | 13.6 |
| B3 | 37 | 20% | 2.2 | 1 |
| C1 | 30 | 20% | 1.4 | 5.2 |
| C2 | 30 | 66% | 1.6 | 4 |
| C3 | 37 | 66% | 3 | 6 |

Example 3. Predicting Bacterial Defiance With a Dimensionless Parameter

Results:

Having demonstrated that bacteria exposed to a prodrug exhibit a binary outcome—susceptibility (i.e., death) or defiance (i.e., survival)—it was next determined whether the behavior could be quantified by a metric of resistance that could be generalized across broad treatment conditions. Based on the model and experimental validation, it was observed that under defiance, populations of live bacteria expanded (i.e., positive growth rate) throughout the course of treatment, which implied that key bacterial growth parameters (e.g., r, $B_{max}$) were greater in value than enzyme-driven death rate parameters (e.g., $k_{cat}$, $K_m$) (FIGS. 3B-3J, 4A-4B). Therefore, to derive a metric to discriminate between defiant and susceptible bacteria, Buckingham Pi theorem was used to identify a dimensionless quantity that represents the competing balance between growth rate and enzymatic turnover, which we defined as the Bacterial Advantage Heuristic (B.A.H.) (Equation 1.2).

$$BAH = \log_{10}\left(\frac{r}{k_{cat}}\right) \quad \text{(Equation 1.2)}$$

Figure 4A:
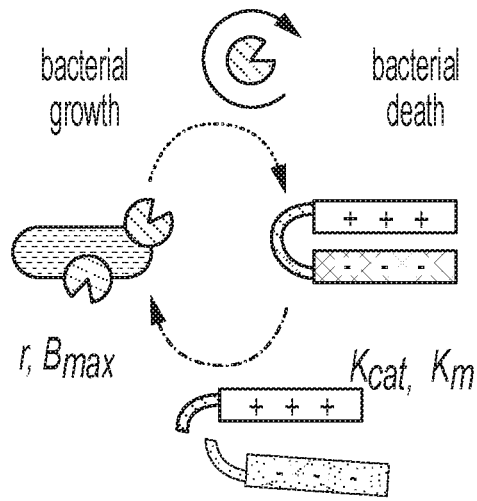
FIG. 4A is a schematic depicting competing rates between bacteria growth, prodrug activation, and bacteria death with the relevant parameters.
Figure 4B:
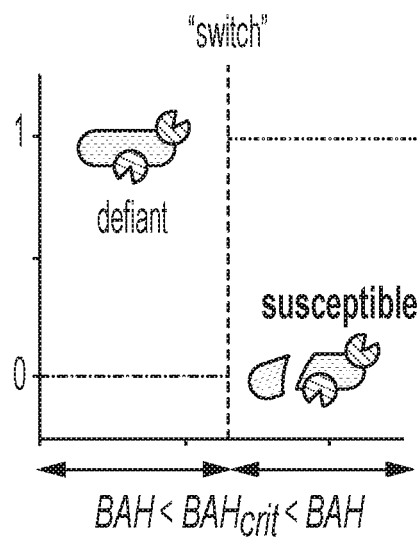
FIG. 4B is an illustrative graph showing the "switch" like behavior that occurs at a critical BAH ($BAH_{crit}$) threshold (bacterial defiance=1 when BAH>$BAH_{crit}$, susceptibility=0 when BAH<$BAH_{crit}$)
Figure 4C:
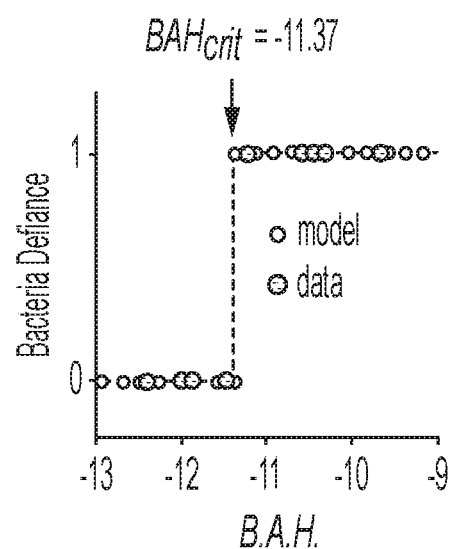
FIG. 4C is a graph showing model prediction (dashed line) and experimental validation (gray dots) of bacteria outcome as a function of BAH to validate the critical defiance value $BAH_{crit}$.
Figure 4D:
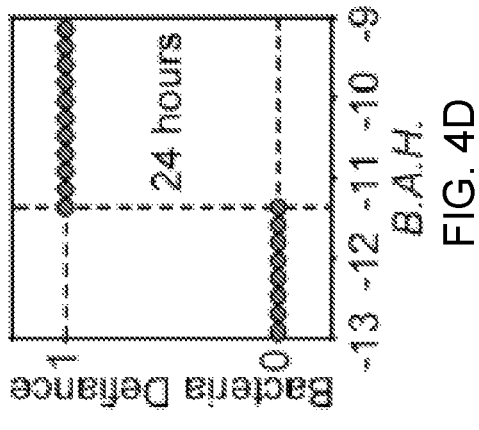
FIGS. 4D-4F are graphs showing model simulations of bacteria outcome as a function of BAH for treatment durations 24, 48, and 72 hours.
Figure 4E:
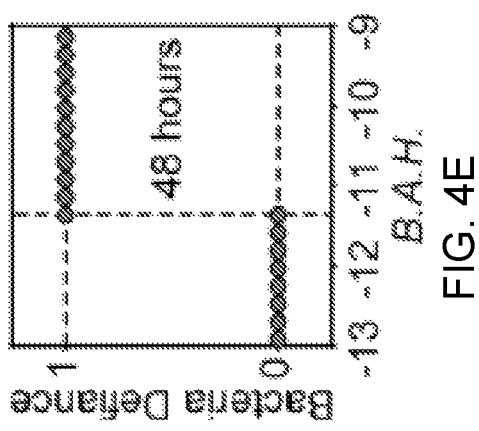
Figure 4F:
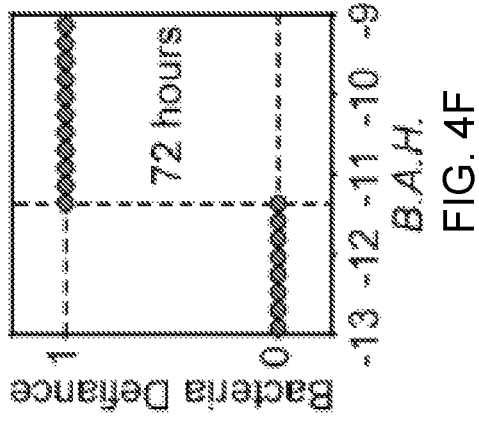
Figure 4G:
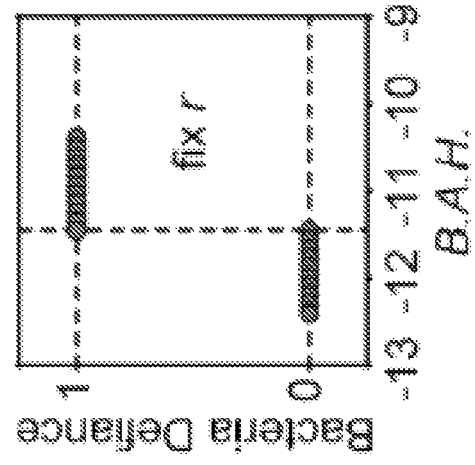
FIGS. 4G-4H and 4J-4K are graphs showing model simulations of bacteria outcome versus BAH by controlling four parameters: r, $k_{cat}$, $K_m$, and $B_{max}$. In each panel, one of these four variables is fixed while the others are changing.
Figure 4H:
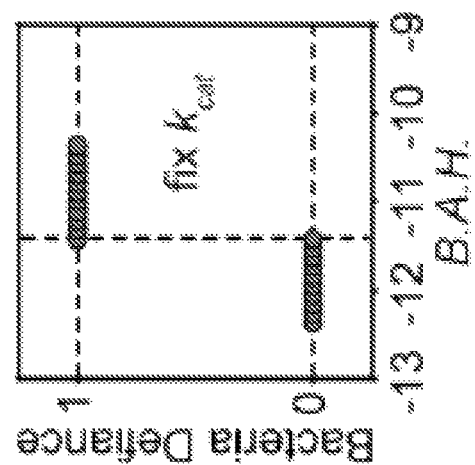
Figure 4I:
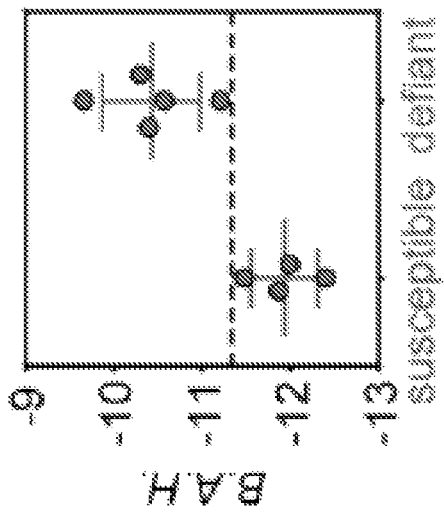
FIG. 4I is a graph classifying bacteria into defiant and susceptible populations based on BAH.
Figure 4L:
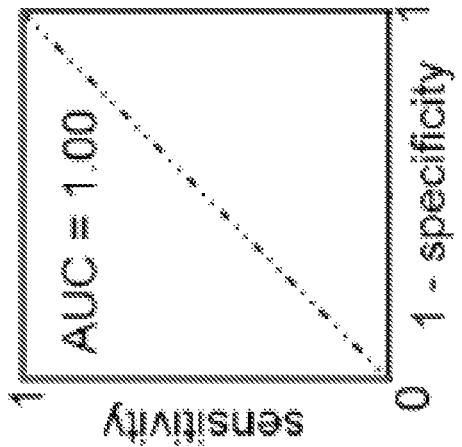
FIG. 4L is a graph showing receiver-operating characteristic (ROC) analysis using BAH to classify populations as defiant based on bacteria-driven parameters (r and $k_{cat}/K_m$).
Figure 4K:
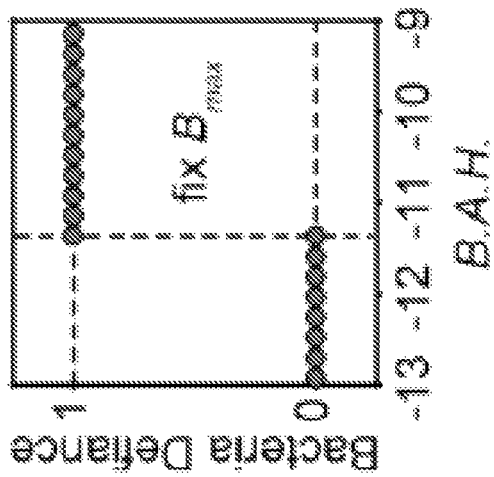
Figure 4J:
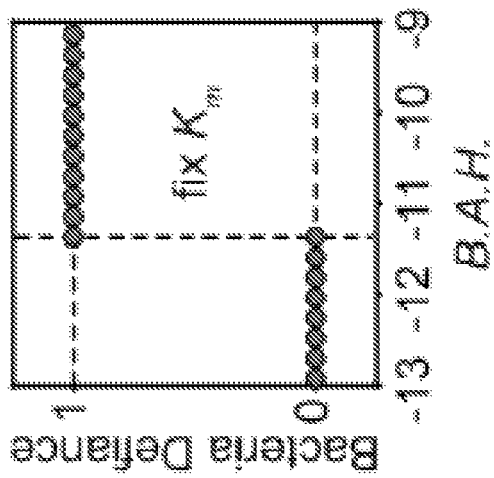
Figure 6A:
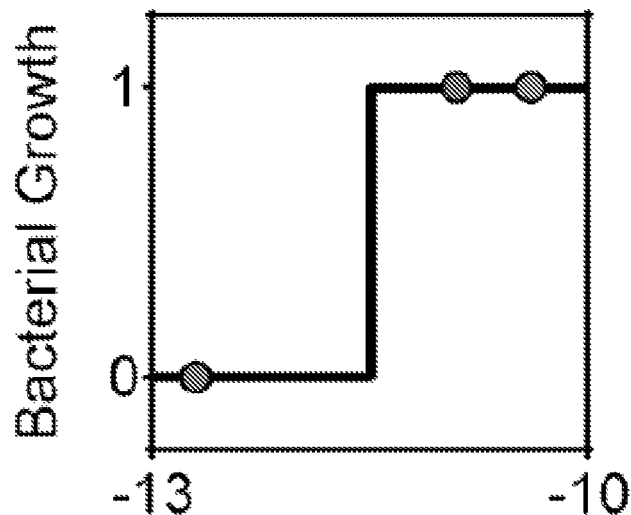
FIG. 6A is a graph showing results of a bacteria viability assay post 24 hour incubation with drug unlocked by various substrates. Bacterial growth=1 if colonies were present after plating, and bacterial growth=0 if there were no colonies present (n=3). B.A.H. values extrapolated from bacteria+ probe velocity measurements fitted to model.
Figure 6B:
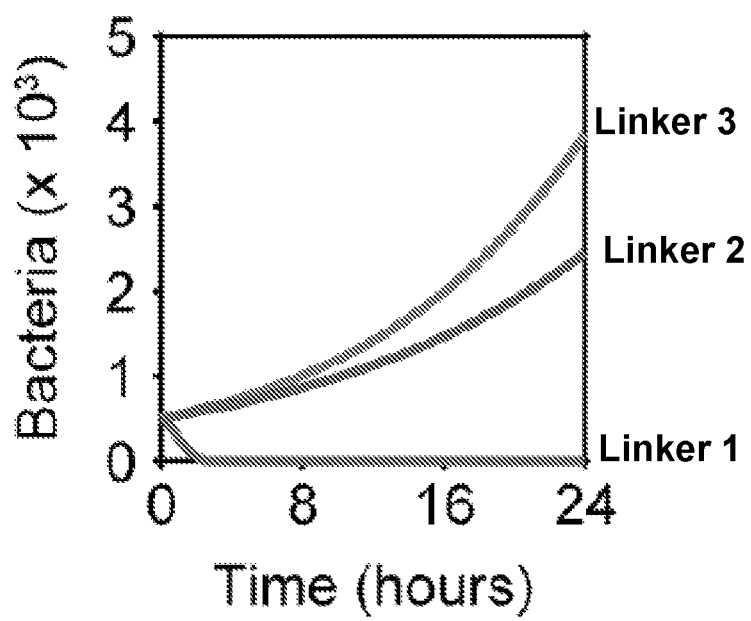
FIG. 6B is a graph showing bacteria dynamics predicted by model given three different enzyme kinetics. Linker 1=RRSRRV (SEQ ID NO:1), Linker 2=RKTR (SEQ ID NO:2), Linker 3=ENLYFQG (SEQ ID NO:3).

This quantity reflects that bacteria have a higher probability of switching to the defiance phenotype under conditions that promote a faster growth rate, r, and slower enzymatic activity, $k_{cat}$. To predict the onset of the defiance phenotype, we sought to determine the critical B.A.H. value that distinguishes defiant bacteria from susceptible populations. Using the mathematical model, >2000 prodrug treatment conditions were simulated covering a range of values for r, $B_{max}$, $k_{cat}$, and $K_m$ and identified a critical value of BAH at which bacteria switch from susceptibility to defiance ($BAH_{crit}$~−11.37) (FIG. 4C). In other words, for any environmental or genetic condition that produces a $BAH > BAH_{crit}$, the bacteria will survive the prodrug treatment, and for $BAH < BAH_{crit}$, the bacteria will die. To test the robustness of this switch-like behavior, treatment outcomes were modeled by varying bacterial growth rates (r) and enzymatic efficiencies ($k_{cat}$) (>100 points) and found that $BAH_{crit}$ was time-independent across a range of prodrug treatment durations. (FIGS. 4D-4F). Additionally, to demonstrate that $BAH_{crit}$ is independent from any system parameter, treatment outcomes (>500 points) were modeled by individually fixing each of the four parameters (i.e., r, $B_{max}$, $k_{cat}$, and $K_m$) in turn and found that $BAH_{crit}$ was invariant across all conditions tested (FIGS. 4G-4K). To confirm the value of $BAH_{crit}$ experimentally, the nine experimental conditions previously tested (A1-3, B1-3, C1-3) were used to fit the values for $k_{cat}$ and r (FIGS. 5A-5J), and then used the computationally-derived critical BAH threshold to classify the phenotype of nine bacteria-prodrug treatment conditions. By receiver-operating-characteristic (ROC) analysis, $BAH_{crit}$ perfectly predicted the onset of defiance (FIGS. 4I, 4L; AUROC=1.00, n=9) with 100% specificity and sensitivity. The model results predicted that changing key system parameters to decrease the B.A.H. below the critical threshold will result in successful treatment of defiant bacteria. To demonstrate this, three different AMP prodrugs with distinct linker sequences (Table 1) with increasing $k_{cat}$ values for OmpT were used to decrease the BAH below $BAH_{crit}$, which allowed for successful treatment of previously defiant populations of bacteria (FIGS. 6A-6B). These findings are important for the successful design and administration of prodrug therapies, which may be improved by optimizing fundamental pharmacokinetic parameters.

Example 4. Combating Bacterial Defiance With Prodrug Biological Circuits

Figure 7A:
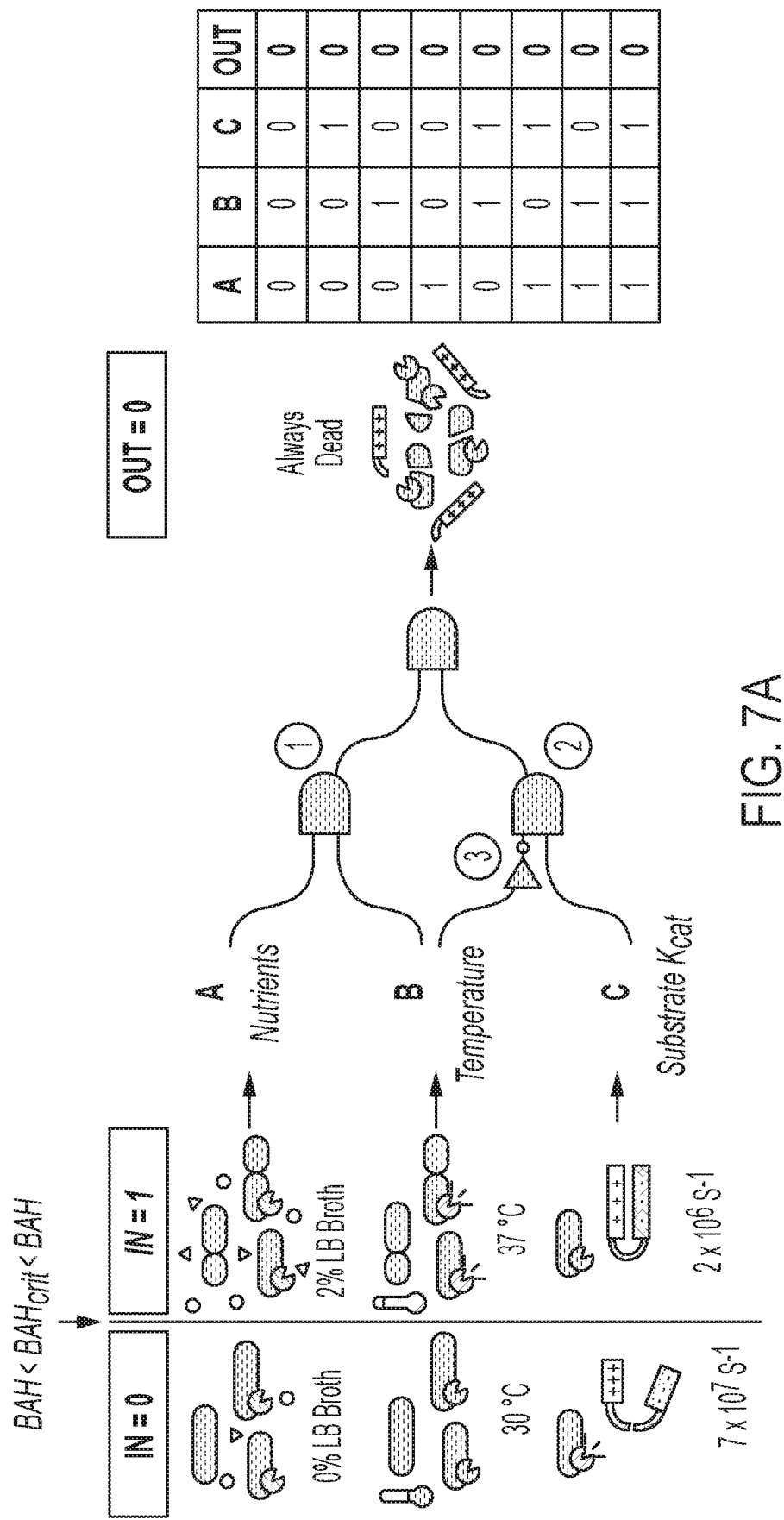
FIG. 7A is a logic circuit schematic depicting a function that universally outputs 0 for all possible combinations of three binary inputs. Inputs are controlled by environmental variables including bacterial nutrients (circles and triangles), ambient temperature (thermometers), and substrate specificity (red substrate=high specificity, blue substrate=low specificity). Depicted parameter values represent experimental conditions. Truth table for universal circuit input-output combinations.
Figure 7B:
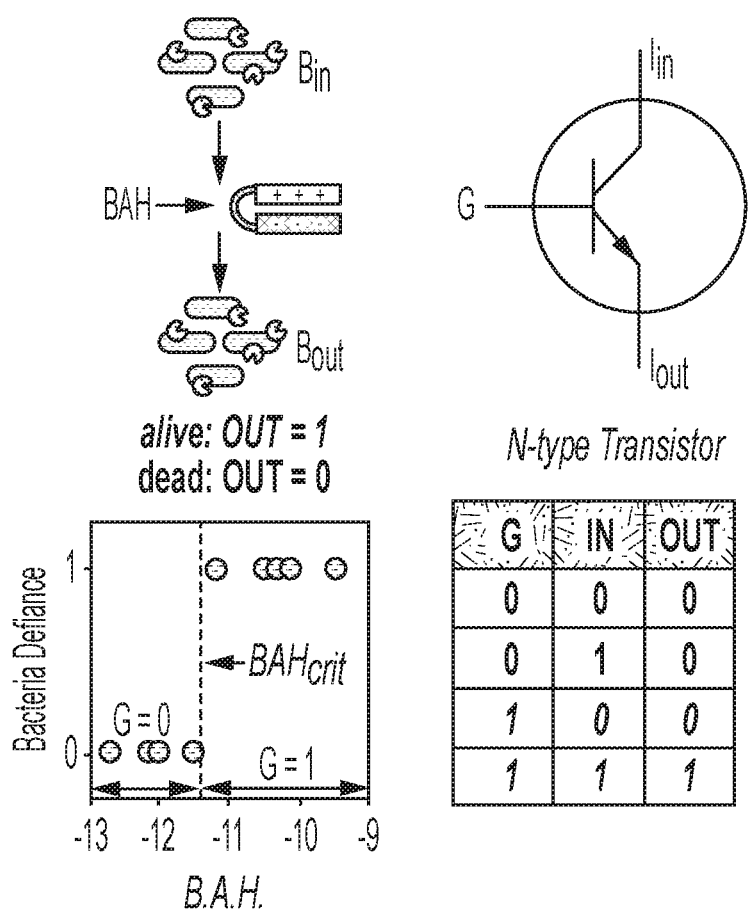
FIG. 7B is a schematic and truth table showing how the AMP prodrug behaves analogously to N-type transistors. Electronic N-type transistors allow the input current ($I_{in}$) to pass when the gate voltage (G) is high. Similarly, the N-type prodrug transistor allows the input bacteria ($B_{in}$) to survive when the gate signal (G) is high (i.e., G=1 when BAH>$BAH_{crit}$).
Figure 7C:
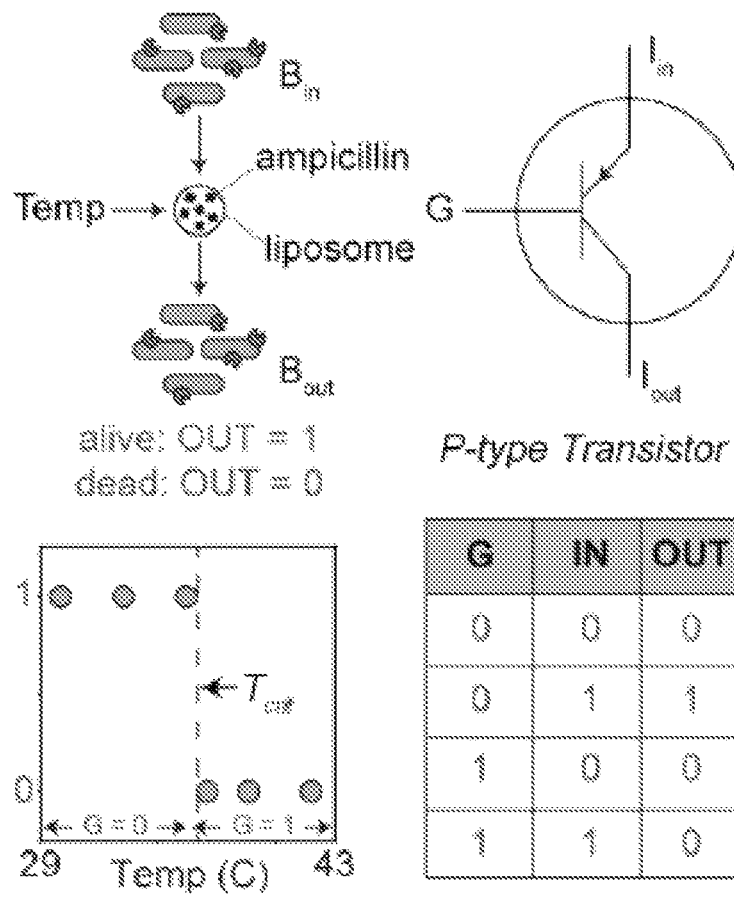
FIG. 7C is a schematic and truth table showing how the heat-triggered, drug loaded liposomes behave analogously to P-type transistors. Electronic P-type transistors allow the input current ($I_{in}$) to pass when the gate voltage (G) is low. Similarly, heat-triggered, drug-loaded liposomes allow the input bacteria ($B_{in}$) to survive ($B_{out}$=1) when the gate signal (G) is low (i.e., G=0 when temperature <$T_{crit}$). All truth tables depict binary input-output combinations.
Figure 8A:
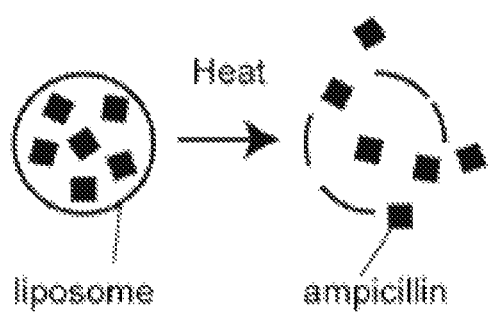
FIG. 8A is a schematic depicting the function of heat-triggered, drug loaded liposomes. Circles represent liposomes, black squares represent drug (ampicillin).
Figure 8B:
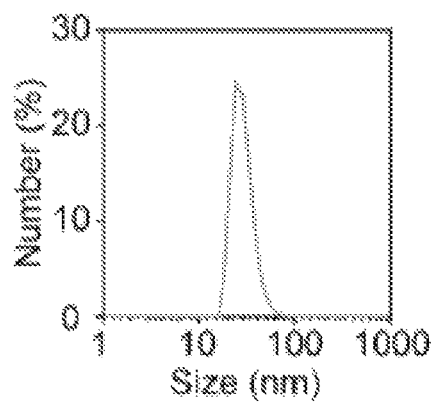
FIG. 8B is a graph showing the results of dynamic light scattering of liposome formulation to determine particle size (~35 nm). Histogram is plotted as the mean of independent measurements (n=3).
Figure 8C:
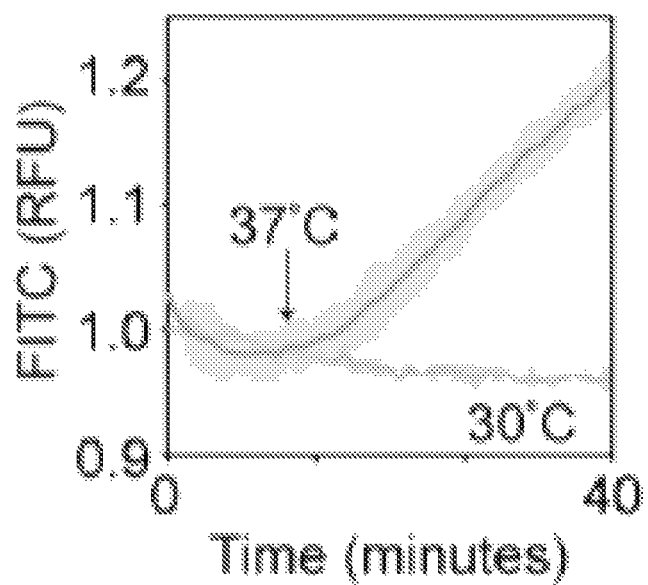
FIG. 8C is a graph showing the results of a fluorescent assay measuring the heat-triggered release of liposome contents. Liposomes were loaded with 100 mM FITC, and heated from 25° C. to 37° C. (indicated by arrow). Grey line represents 30° C. control. Lines are plotted as means of independent measurements, shading represents standard deviation (n=3).
Figure 8D:
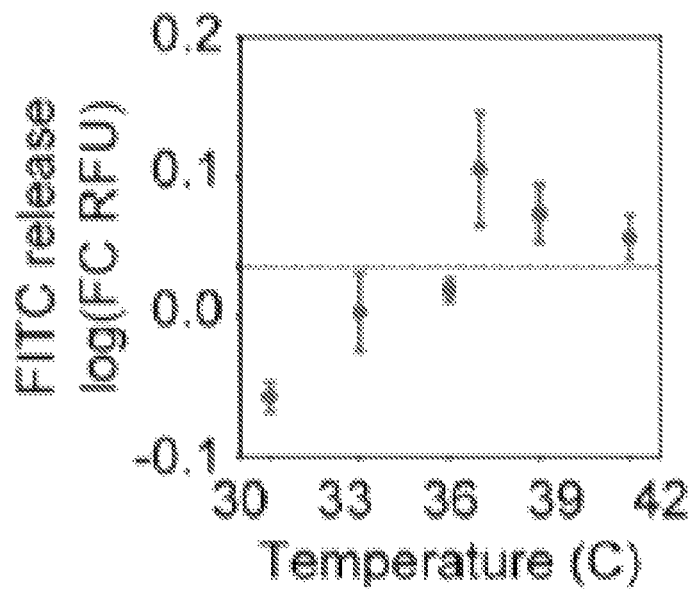
FIG. 8D is a graph showing the results of a fluorescent assay measuring the release of FITC from heat triggered liposomes at various temperatures. All samples were heated to 30° C. for 10 minutes, then heated at the plotted temperature for 30 minutes. Measurements are plotted as fold change in RFU between final measurement and measurement at 30° C. Error bars represent standard deviation (n=3).

Results:

The model revealed that bacterial defiance arises during prodrug monotherapy when environmental parameters, as represented by a dimensionless constant, cross a critical transition BAH value. To combat bacterial defiance, a multi-prodrug approach was designed to eliminate defiant bacteria that would otherwise resist treatment to a single prodrug (FIG. 7A). To do this, it was recognized that the bacterial switch from susceptibility to defiance could be considered as behaving analogously to electronic transistors—transistors allow input current ($I_{in}$) to pass ($I_{out}$) when the gate voltage (G) crosses a threshold, whereas with AMP prodrugs, input bacteria ($B_{in}$) survive treatment ($B_{out}$) when the BAH (gate) crosses a critical value (FIG. 7B). Under this analogy, it was postulated that multiple prodrug biological transistors could be used to construct logical operations (i.e., AND, OR, NOT gates) that allow for the design of integrated biological circuits that output state "0" (i.e., bacterial death) for all possible inputs. These biological circuits would then be representative of a multi-prodrug strategy to eliminate bacteria even when input BAH variables (i.e., temperature, nutrient level, enzyme activity) would result in a state of defiance for a single prodrug. To accomplish this, complementary N-type and P-type transistors were designed, which are required to construct all possible logic gates (Amos and James, Principles of Transistor Circuits (2000)). N-type transistors allow input current to pass when the gate signal is above a defined threshold, whereas P-type transistors allow current to pass when the gate signal is below a defined threshold. N-type transistors were constructed with the AMP prodrug system, which allowed input bacteria ($B_{in}=1$) to survive ($B_{out}=1$) when the BAH is above $BAH_{crit}$ which was used to define the gate threshold (i.e., $BAH>BAH_{crit}$ equivalent to $G=1$; $BAH<BAH_{crit}$ equivalent to $G=0$) (FIG. 7B). To create P-type transistors, heat-triggered liposomes were synthesized (Needham, et al, Cancer Research, 60:1197-1201 (2000)) (FIGS. 8A-8D) and loaded with the antibiotic ampicillin (Thonus, et al., Antimicrobial Agents and Chemotherapy, 22:386-390 (1982)), which was released at temperatures above 37° C. to kill bacteria (i.e., $B_{out}=0$) (FIG. 7C). Above this critical temperature, treatment with AMP prodrugs leads to bacterial defiance (i.e., $BAH>BAH_{crit}$ or $G=1$) and E. coli survive prodrug treatment by proliferating significantly faster than prodrug activation (Farewell, and Neidhart, Journal of Bacteriology, 180:4704-4710 (1998)). Temperatures above 37° C. were defined as corresponding to $G=1$ and temperatures below above 37° C. were defined as $G=0$ for the P-type biological transistor to match inverse gate values for the N-type biological transistor. These results demonstrated that antimicrobial drugs could be modeled with similar input and output characteristics compared to N-type and P-type transistors.

Figure 9H:
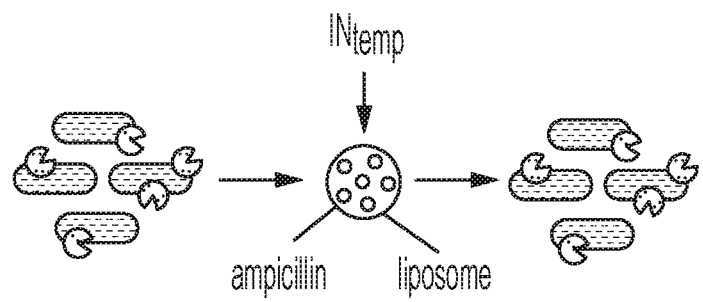
FIGS. 9H-9J show a bacterial viability assay validating the function of a prodrug-based NOT gate.
Figure 9I:
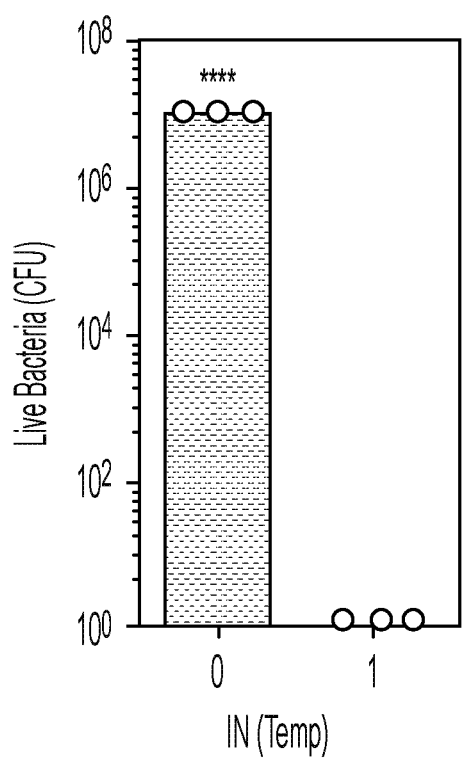
Figure 9J:
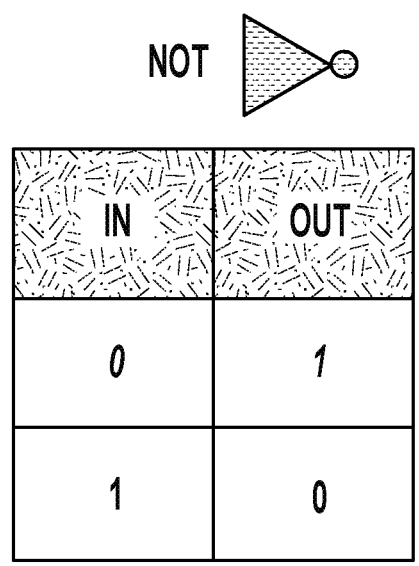
Figure 9K:
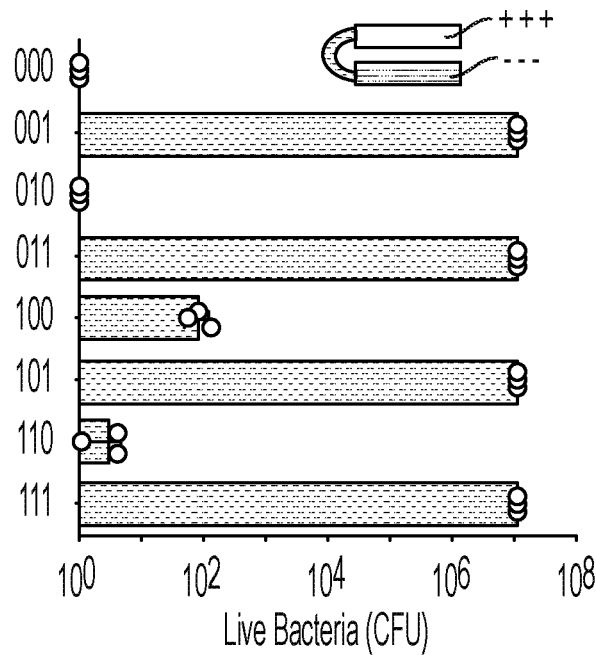
FIG. 9K is a graph showing the results of a bacterial viability assay quantifying the outcome of a single prodrug in the context of different environmental conditions.
Figure 9L:
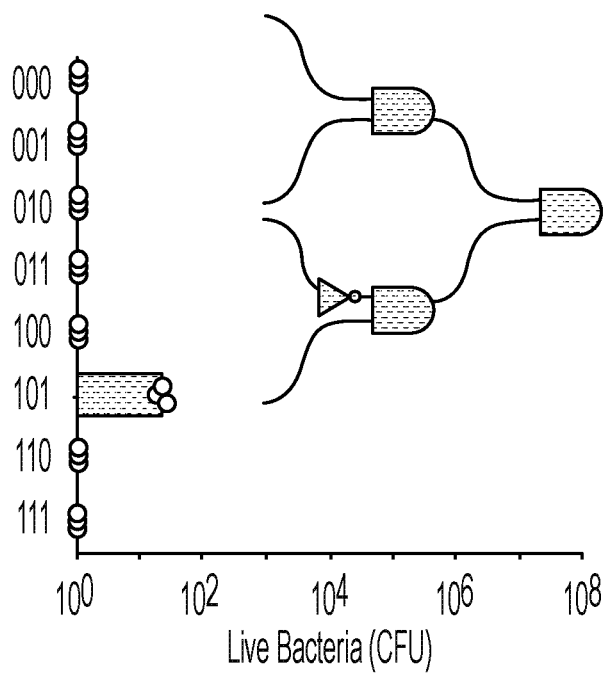
FIG. 9L is a graph showing the results of a bacterial viability assay demonstrating the eight outputs of the autonomous circuit.

To demonstrate the use of multiple prodrug transistors in biological circuits capable of killing defiant bacteria, three variables (i.e., bacterial nutrients, temperature, linker substrate $k_{cat}$) were selected that independently influence bacteria-prodrug competition to act as circuit inputs (i.e., A, B, and C respectively). For each circuit input, the value 0 or 1 was assigned by fixing all other variables and choosing one condition that enabled bacterial survival (i.e., IN=1 when $BAH>BAH_{crit}$) and one condition that resulted in bacterial death (i.e., IN=0 when $BAH<BAH_{crit}$). A biological circuit was designed to kill bacteria (i.e., OUT=0) under all eight combinations of nutrient (LB Broth=0% or 2%), temperature (T=30° C. or 37° C.), and linker substrate ($k_{cat}=7\times10^7$ s$^{-1}$ or $2\times10^6$ s$^{-1}$) conditions while using three AND gates and one NOT gate (FIG. 7A). Electronic AND gates are created by placing two transistors in series; similarly, bacteria were sequentially dosed with two prodrugs, each with corresponding BAH values to represent the gate inputs (i.e., A and B). The corresponding BAH value was controlled for each prodrug with the linker substrate sequence (e.g., A or B=0 when $k_{cat}$ $7\times10^7$ s$^{-1}$, A or B=1 when $k_{cat}=2\times10^6$ s$^{-1}$) and tested all four combinations of the two prodrugs (i.e., AB=00, 01, 10, and 11). When exposed to all four possible inputs, bacteria only survived the condition with two low $k_{cat}$ prodrugs (i.e., AB=11), which matched the ideal outputs of an AND gate (FIGS. 9E-9G). These results show that dosing multiple prodrugs in sequence reduces the fraction of bacterial populations that survive (e.g., one prodrug=50% survival, two prodrugs=25% survival, etc.). Whereas the AND gate included prodrugs in series, the implementation of an OR gate was demonstrated by splitting a population of bacteria in half (i.e., separate wells), dosing each with a different prodrug during the same time interval (i.e., in parallel) and recombining the bacteria post-treatment. Using this circuit, bacteria survived in any case where at least one half of the population was dosed with low $k_{cat}$ prodrug (i.e., AB=01, 10, or 11), matching the ideal outputs of an OR gate (FIGS. 9H-9J). A NOT gate was created by using a P-type transistor including ampicillin-loaded heat-triggered liposomes, which caused bacteria to die at high temperatures (i.e., IN=1) and survive at low temperatures (i.e., IN=0). (FIG. 9K). These results show that heat-triggered liposomes can be used as a fail-safe to kill bacteria above the critical temperature representing the onset of the defiance phenotype. To validate the multi-prodrug circuit, populations of bacteria were incubated under each of the eight environmental conditions with three prodrugs: (1) an AMP prodrug with fixed $k_{cat}/K_m$, (2) an AMP prodrug with $k_{cat}/K_m$ determined by input C, and (3) a heat-triggered, drug-loaded liposome (FIG. 7A). Whereas a single prodrug only eliminated bacteria in half of the input cases (FIG. 9L), the circuit autonomously eliminated bacteria under all eight combinations of the three environmental signals. These results demonstrate that by utilizing the transistor-like properties of prodrugs, biocircuits that combat bacterial defiance can be designed and administered.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method for improving prodrug treatment comprising:
identifying a dimensionless quantity of the prodrug to discriminate between successful treatment and unsuccessful treatment of a subject with the prodrug, wherein identifying the dimensionless quantity comprises using mathematical modeling to determine a metric threshold wherein the growth or survival of infectious agents in the presence of the prodrug outweighs the activity of the prodrugs;
assigning a value to the prodrug by modeling the infectious agents' response to the prodrug, wherein prodrugs having a modeled value greater than the metric threshold are deemed unsuccessful and prodrugs having a modeled value less that the metric threshold are deemed successful, and
administering the prodrug to the subject in need thereof if the prodrug has a modeled value less than the metric threshold.

2. The method of claim 1, wherein identifying the dimensionless quantity of the prodrug further comprises determining environmental and genetic conditions in which the infectious agents are unresponsive to a prodrug composition.

3. The method of claim 1, wherein the prodrug is an antibacterial prodrug and the infectious agent is bacteria.

4. The method of claim 3, wherein the mathematical modeling uses the equation $$BAH = \log_{10}\left(\frac{r}{k_{cat}}\right),$$

wherein r is the growth rate of the bacteria and $k_{cat}$ is the catalytic turnover rate of the prodrug.

5. A method of treating a subject in need thereof, comprising,
identifying a dimensionless quantity of each prodrug of a plurality of prodrugs to discriminate between successful treatment and unsuccessful treatment of a subject with the prodrug, wherein identifying the dimensionless quantity comprises using mathematical modeling to determine a metric threshold wherein the growth or survival of infectious agents in the presence of the prodrug outweighs the activity of the prodrugs;
assigning a value to the prodrug by modeling the infectious agents' response to the prodrug, wherein prodrugs having a modeled value greater than the metric threshold are deemed unsuccessful and prodrugs having a modeled value less that the metric threshold are deemed successful, and
selecting two or more prodrugs for administration to the subject wherein the two or more prodrugs have modeled values covering a range of values, and
administering the two or more prodrugs to the subject such that there is increased infectious agent killing when the two or more prodrugs are administered in comparison to administration of a single prodrug.

6. The method of claim 5, wherein the prodrugs comprise an antimicrobial peptide conjugated to a polymer by a cleavable bond or cleavable linker, wherein the antimicrobial peptide has little or no antimicrobial activity while conjugated to the polymer and has antimicrobial activity when not bound to the polymer.

7. The method of claim 5, wherein the amount of each prodrug composition administered to the subject comprises 0.1 mg to 2000 mg of the prodrug.

8. The method of claim 5, wherein the subject has a bacterial infection caused by a bacterium selected from the group consisting of *Escherichia coli, Streptococcus, Staphylococcus, Corynebacterium, Listeria, Bacillus, Clostridium, Salmonella enteritidis, Salmonella typhi, Shigella, Pseudomonas aeruginosa, Helicobater, Stenotrophomonas, Bdellovibrio, Legionella pneumophila, Vibrio cholera, Neisseria gonorrhoeae, Neisseria meningitidis, Moraxella catarrhalis, Haemophilis influenza, Chlamydia trachomatis, Yersinia pestis, Klebsiella pneumoniae, Proteus mirabilis, Enterobacter cloacae, Serratia marcescens* and *Acinetobacter baumannii*.

* * * * *

SEQUENCE LISTING

<160> NUMBER OF SEQ ID NOS: 17

<210> SEQ ID NO 1
<211> LENGTH: 6
<212> TYPE: PRT
<213> ORGANISM: Escherichia coli

<400> SEQUENCE: 1

Arg Arg Ser Arg Arg Val
1               5

<210> SEQ ID NO 2

```
<211> LENGTH: 4
<212> TYPE: PRT
<213> ORGANISM: Escherichia coli

<400> SEQUENCE: 2

Arg Lys Thr Arg
1

<210> SEQ ID NO 3
<211> LENGTH: 7
<212> TYPE: PRT
<213> ORGANISM: Tobacco etch virus

<400> SEQUENCE: 3

Glu Asn Leu Tyr Phe Gln Gly
1               5

<210> SEQ ID NO 4
<211> LENGTH: 14
<212> TYPE: PRT
<213> ORGANISM: Unknown
<220> FEATURE:
<223> OTHER INFORMATION: Bacterial protease substrate

<400> SEQUENCE: 4

Lys Leu Ala Lys Leu Ala Lys Lys Leu Ala Lys Leu Ala Lys
1               5                   10

<210> SEQ ID NO 5
<211> LENGTH: 6
<212> TYPE: PRT
<213> ORGANISM: Unknown
<220> FEATURE:
<223> OTHER INFORMATION: Bacterial protease

<400> SEQUENCE: 5

Asn Leu Tyr Phe Gln Gly
1               5

<210> SEQ ID NO 6
<211> LENGTH: 4
<212> TYPE: PRT
<213> ORGANISM: Unknown
<220> FEATURE:
<223> OTHER INFORMATION: Bacterial protease

<400> SEQUENCE: 6

Leu Leu Val Tyr
1

<210> SEQ ID NO 7
<211> LENGTH: 5
<212> TYPE: PRT
<213> ORGANISM: Unknown
<220> FEATURE:
<223> OTHER INFORMATION: Bacterial protease

<400> SEQUENCE: 7

Arg Leu Arg Gly Gly
1               5

<210> SEQ ID NO 8
<211> LENGTH: 4
<212> TYPE: PRT
<213> ORGANISM: Unknown
<220> FEATURE:
<223> OTHER INFORMATION: Bacterial protease
```

```
<400> SEQUENCE: 8

Ala Ala Pro Val
1

<210> SEQ ID NO 9
<211> LENGTH: 4
<212> TYPE: PRT
<213> ORGANISM: Unknown
<220> FEATURE:
<223> OTHER INFORMATION: Bacterial protease

<400> SEQUENCE: 9

Asp Val Glu Asp
1

<210> SEQ ID NO 10
<211> LENGTH: 5
<212> TYPE: PRT
<213> ORGANISM: Unknown
<220> FEATURE:
<223> OTHER INFORMATION: Bacterial protease

<400> SEQUENCE: 10

Gly Pro Leu Gly Pro
1               5

<210> SEQ ID NO 11
<211> LENGTH: 8
<212> TYPE: PRT
<213> ORGANISM: Unknown
<220> FEATURE:
<223> OTHER INFORMATION: Bacterial protease

<400> SEQUENCE: 11

Asp Glu Phe Ile Ala Asp Cys Glu
1               5

<210> SEQ ID NO 12
<211> LENGTH: 8
<212> TYPE: PRT
<213> ORGANISM: Unknown
<220> FEATURE:
<223> OTHER INFORMATION: Bacterial protease

<400> SEQUENCE: 12

Lys Pro Leu Gly Met Trp Ser Arg
1               5

<210> SEQ ID NO 13
<211> LENGTH: 28
<212> TYPE: PRT
<213> ORGANISM: Artificial Sequence
<220> FEATURE:
<223> OTHER INFORMATION: Synthetic construct

<400> SEQUENCE: 13

Glu Glu Glu Glu Glu Glu Glu Glu Glu Glu Glu Glu Glu Arg Arg Ser
1               5                   10                  15

Arg Arg Val Arg Arg Arg Arg Arg Arg Arg Arg
            20                  25

<210> SEQ ID NO 14
<211> LENGTH: 23
<212> TYPE: PRT
<213> ORGANISM: Artificial Sequence
```

```
<220> FEATURE:
<223> OTHER INFORMATION: Synthetic construct

<400> SEQUENCE: 14

Glu Glu Glu Glu Glu Glu Glu Glu Glu Glu Glu Arg Lys Thr Arg Arg
1               5                   10                  15

Arg Arg Arg Arg Arg Arg Arg
            20

<210> SEQ ID NO 15
<211> LENGTH: 24
<212> TYPE: PRT
<213> ORGANISM: Artificial Sequence
<220> FEATURE:
<223> OTHER INFORMATION: Synthetic construct

<400> SEQUENCE: 15

Glu Glu Glu Glu Glu Glu Glu Glu Glu Asn Leu Tyr Phe Gln Gly Arg
1               5                   10                  15

Arg Arg Arg Arg Arg Arg Arg Arg
            20

<210> SEQ ID NO 16
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term DABCYL fluorophore
<220> FEATURE:
<221> NAME/KEY: MOD_RES
<222> LOCATION: (29)..(29)
<223> OTHER INFORMATION: Lys(5-FAM) quencher

<400> SEQUENCE: 16

Glu Glu Glu Glu Glu Glu Glu Glu Glu Glu Glu Glu Glu Arg Arg Ser
1               5                   10                  15

Arg Arg Val Arg Arg Arg Arg Arg Arg Arg Arg Lys
            20                  25

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term DABCYL fluorophore
<220> FEATURE:
<221> NAME/KEY: MOD_RES
<222> LOCATION: (7)..(7)
<223> OTHER INFORMATION: Lys(5-FAM) quencher

<400> SEQUENCE: 17

Arg Arg Ser Arg Arg Val Lys
1               5
```